(12) United States Patent
Scheperjans et al.

(10) Patent No.: US 11,906,517 B2
(45) Date of Patent: *Feb. 20, 2024

(54) METHOD FOR DIAGNOSTICS, TREATMENT AND PREVENTION OF PARKINSON'S DISEASE

(71) Applicant: Neurobiome Oy, Helsinki (FI)

(72) Inventors: Filip Scheperjans, Helsinki (FI); Petri Auvinen, Helsinki (FI); Velma Aho, Helsinki (FI); Pedro Pereira, Helsinki (FI); Kaisa Koskinen, Graz (AT); Lars Paulin, Helsinki (FI)

(73) Assignee: Neurobiome Oy, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 17/933,952

(22) Filed: Sep. 21, 2022

(65) Prior Publication Data
US 2023/0221314 A1 Jul. 13, 2023

Related U.S. Application Data

(60) Continuation of application No. 17/116,045, filed on Dec. 9, 2020, now Pat. No. 11,499,971, which is a division of application No. 16/186,663, filed on Nov. 12, 2018, now abandoned, which is a division of application No. 15/314,240, filed as application No. PCT/FI2015/050374 on May 28, 2015, now Pat. No. 10,139,408.

(30) Foreign Application Priority Data

May 28, 2014 (FI) ..................... 20145492

(51) Int. Cl.
| | |
|---|---|
| A61K 39/02 | (2006.01) |
| G01N 33/569 | (2006.01) |
| G01N 33/68 | (2006.01) |
| C12Q 1/04 | (2006.01) |
| A61K 35/741 | (2015.01) |

(52) U.S. Cl.
CPC ...... *G01N 33/56911* (2013.01); *A61K 35/741* (2013.01); *C12Q 1/04* (2013.01); *G01N 33/6896* (2013.01); *G01N 2800/2835* (2013.01); *G01N 2800/50* (2013.01); *Y02A 50/30* (2018.01)

(58) Field of Classification Search
None
See application file for complete search history.

(56) References Cited

U.S. PATENT DOCUMENTS

| | | |
|---|---|---|
| 8,580,522 B2 | 11/2013 | Fallon |
| 9,719,144 B2 | 8/2017 | Krajmalnik-Brown et al. |
| 10,137,157 B2 | 11/2018 | Bjorck et al. |
| 11,185,562 B2 | 11/2021 | Cook et al. |
| 2004/0062757 A1 | 4/2004 | Finegold |
| 2004/0170617 A1 | 9/2004 | Finegold |

FOREIGN PATENT DOCUMENTS

| | | |
|---|---|---|
| WO | 2011053653 A2 | 5/2011 |
| WO | 2013036290 A1 | 3/2013 |
| WO | 2013053836 A1 | 4/2013 |
| WO | 2013056222 A1 | 4/2013 |
| WO | 2013176774 A1 | 11/2013 |
| WO | 2013190068 A1 | 12/2013 |

OTHER PUBLICATIONS

Aiheuttavatko bakteerit Parkinsonin taudin? [online] Apr. 9, 2014 (Apr. 9, 2014), [retrieved Aug. 12, 2014]. Retrieved from the Internet: <URL: http://yle.fi/aihe/artikkeli/2014/04/09/aiheuttavatko-bakteerit-parkinsonin-taudin> the whole document, esp. page 1, last two lines-p. 2, first two lines; p. 2, paragraph 4; p. 3, paragraph 2.
Scheperjans, F. et al. Gut microbiota are related to Parkinson's disease and clinical phenotype. Movement Disorders, Mar. 2015, vol. 30, No. 3, pp. 350-358. Available from the Internet Dec. 5, 2014 (Dec. 5, 2014).
Scheperjans, F. et al. Gut microbiota are associated with Parkinson's disease and clinical phenotype—a case-control study. European Journal of Neurology, May 2014, vol. 21, Suppl. 1, Sp. Iss. SI, p. 759, first published online May 28, 2014, DOI: 10.1111/ene.12500.
Scheperjans, F. et al. Gut microbiota are related to Parkinson's disease and clinical phenotype. Movement Disorders, 2014, p. 1-9, published online Dec. 5, 2014 (Dec. 12, 2014) [Epub ahead of print] & database Medline [online] Accession No. 25476529 [retrieved Dec. 10, 2014].
Brenner, S. R. Blue-green algae or cyanobacteria in the intestinal micro-flora may produce neurotoxins such as Beta-N-Methylamino-1-Alanine (BMAA) which may be related to development of amyotrophic lateral sclerosis, Alzheimer's disease and Parkinson-Dementia-Complex in humans and Equine Motor Neuron Disease in Horses. Medical Hypotheses, Jan. 2013, vol. 80, No. 1, p. 103.

(Continued)

*Primary Examiner* — Jennifer E Graser
(74) *Attorney, Agent, or Firm* — Banner & Witcoff, Ltd.

(57) ABSTRACT

The present invention relates to the field of medicine and in particular to Parkinson's disease (PD). Specifically the present invention relates to methods and means for early detection of PD. The invention relates also to methods and means for treatment or prophylaxis of PD.

In the method of the invention a probability of a subject developing or having Parkinson's disease (PD) is determined by measuring the relative abundances of one or multiple microbial taxa in a sample from a subject; and the probability of the subject developing or having PD is determined based on the measured abundances. The present invention provides a novel approach for the diagnostics of PD.

15 Claims, 19 Drawing Sheets

Specification includes a Sequence Listing.

(56) References Cited

OTHER PUBLICATIONS

Tan, A. H. et al. Small intestinal bacterial overgrowth in Parkinson's disease. Parkinsonism and Related Disorders, May 2014, vol. 20, No. 5, pp. 535-540. Available from the Internet Mar. 2, 2014 (Mar. 2, 2014).
Derkinderen, P. et al. Gut feelings about smoking and coffee in Parkinson's disease. Movement' Disorders, Jul. 2014, vol. 29, No. 8, pp. 976-979. Available from the Internet Apr. 21, 2014 (Apr. 21, 2014).
Labus J. et al. Human Gut Microbial Clusters Correlate with Anatomical Brain Signatures: A Pilot Study. Biological Psychiatry, May 1, 2014 (May 1, 2014), vol. 75, No. 9, Supplement, p. 225S, abstract 77 6.
Lane DJ. 16S/23S rRNA sequencing. In: Stackebrandt,E. Goodfellow,M. Eds. Nucleic Acid Techniques in Bacterial Systematics. 1991; p. 115-175.
Savica R, Carlin JM, Grossardt BR et al. Medical records documentation of constipation preceding parkinson disease: A case-control study. Neurology 2009;73(21):1752-1758.
Noyce AJ, Bestwick JP, Silveira-Moriyama L et al. Meta-analysis of early nonmotor features and risk factors for parkinson disease. Ann Neurol 2012;72(6):893-901.
Kieburtz K, Wunderle KB. Parkinson's disease: Evidence for environmental risk factors. Mov Disord 2013;28(1):8-13.
De Vos WM, de Vos EA. Role of the intestinal microbiome in health and disease: From correlation to causation. Nutr Rev 2012;70 Suppl 1:S45-56.
Segata N, Izard J, Waldron L, Gevers D, Miropolsky L, Garrett WS, Huttenhower C. Metagenomic biomarker discovery and explanation. Genome Biol. Jun. 24, 2011;12(6):R60. doi: 10.1186/GB-2011-12-6-r60.
Arumugam M, Raes J, Pelletier E et al. Enterotypes of the human gut microbiome. Nature 2011;473(7346):174-180.
Jankovic J, McDermott M, Carter J et al. Variable expression of parkinson's disease: A base-line analysis of the DATATOP cohort. the parkinson study group. Neurology 1990;40(10):1529-1534.
Poletti M, Frosini D, Pagni C et al. The association between motor subtypes and alexithymia in de novo parkinson's disease. J Neurol 2011;258(6):1042-1045.
Edwards U, Rogall T, Blocker H et al. Isolation and direct complete nucleotide determination of entire genes. characterization of a gene coding for 16S ribosomal RNA. Nucleic Acids Res 1989;17(19):7843-7853.
Schloss PD, Westcott SL, Ryabin T et al. Introducing mothur: Open-source, platform-independent, community-supported software for describing and comparing microbial communities. Appl Environ Microbiol 2009;75(23):7537-7541.
White JR, Nagarajan N, Pop M. Statistical methods for detectingdifferentially abundant features in clinical metagenomic samples. PLoS Comput Biol 2009;5:e1000352.

Fasano, A. et al., The Role of Small Intestinal Bacterail Overgrowth in Parkinson's Disease, Movement Disorders, 2013, vol. 28, No. 9, pp. 1241-1249.
Nielsen, H. H., Treatment for Helicobacter pylori infection and risk of parkinson's disease in Denmark, European Journal of Neurology, 2012, vol. 19, No. 6, pp. 864-869.
Extended European Search Report issued from corresponding EP Patent Application No. 15798909.6, dated Jan. 24, 2018.
Office Action issued for corresponding Finnish Patent Application No. 20145492, dated Mar. 26, 2018.
Tottey, W. et al., The Human Gut Chip "HuGChip", and Explorative Phylogenetic Microarry for Determining Gut Microbiome Diversity at Family Level, PloS One, 2013, vol. 8, No. 5, e62544, pp. 1-12.
Gray (https://www.nutraingredients.com/Article/2017/10/05/Prebiotic-tea-Mouse-data-suggests-black-tea-polyphenols-play-role-in-weight-loss-by-changing-gut-bacteria).
Gniechwitz et al (J. Agric. Food Chem. 2007, 55: 6989-6996).
Carlson et al (Curr Dev Nutr. Mar. 2018; 2(3): nzy005).
https://www.healthline.com/nutrition/19-best-prebiotic-foods.
Jul. 7, 2020—Non-Final Office Action—U.S. Appl. No. 16/186,663.
Yanagisawa et al. "Proteinase Activity of Prevotella Species Associated with Oral Purulent Infection" Current Microbiology, vol. 52, 2006, pp. 375-378.
Zhu et al. "Structural changes in the gut microbiome of constipated patients" Physiol Genomics 46: 679-686, 2014.
Nseir et al., "Prosthetic Septic Arthritis Secondary to Prevotella bivia Bacteremia in a Patient With polymyalgia Rheumatica" Infectious Diseases in Clinical Practice, vol. 16, No. 3, May 2008, pp. 190-191.
Kononen et al. "Pigmented Prevotella species in the periodontally healthy oral cavity" FEMS Immunology and Medical Microbiology, 6 (1993) 201-206.
Glazunova et al. "*Prevotella timonensis* sp. no., isolated from a human breast abscess" International Journal of Systematic and Evolutionary Microbiology (2007), 57, 883-886.
Dec. 7, 2020—(US) Final Office Action—U.S. Appl. No. 16/186,663.
Perez-Pardo "The gut-brain axis in Parkinson's disease: Possibilities for food-based therapies" European Journal of Pharmacology, 817 (2017) 86-95.
Kang et al. "Reduced Incidence of Prevotella and Other Fermenters in Intestinal Microflora of Autistic Children" PLoS One, Jul. 2013, vol. 8, Issue 7, pp. 1-14.
Oct. 11, 2022 (EP) Office Action Application No. 20203903.8.
Greene James G.: "Causes and Consequences of Degeneration of the Dorsal Motor Nucleus of the Vagus Nerve in Parkinson's Disease", Antioxidants and Redox Signaling, vol. 21, No. 4, Aug. 1, 2014 (Aug. 1, 2014), pp. 649-667, XP055968354, US ISSN: 1523-0864, DOI: 10.1089/ars.2014.5859.
Tome et al: "Inflammation and a-Synuclein's Prionlike Behavior in Parkinson's Disease—Is There a Link?", Molecular Neurobiology, vol. 47, No. 2, Apr. 1, 2013 (Apr. 1, 2013), pp. 561-574, XP055968355, New York ISSN: 0893-7648, DOI: 10.1007/s12035-012-8267-8 Retrieved from the Internet: URL:https://www.ncbi.nlm.nih.gov/pmc/articles/PMC3589652/pdf/ 12035_2012_Article_8267.pdf.

| Group | Control | Parkinson | Total |
|---|---|---|---|
| P | 19 | 5 | 24 |
| B | 23 | 21 | 44 |
| R | 30 | 46 | 76 |
| Total | 72 | 72 | 144 |

Chi square
p=0.003

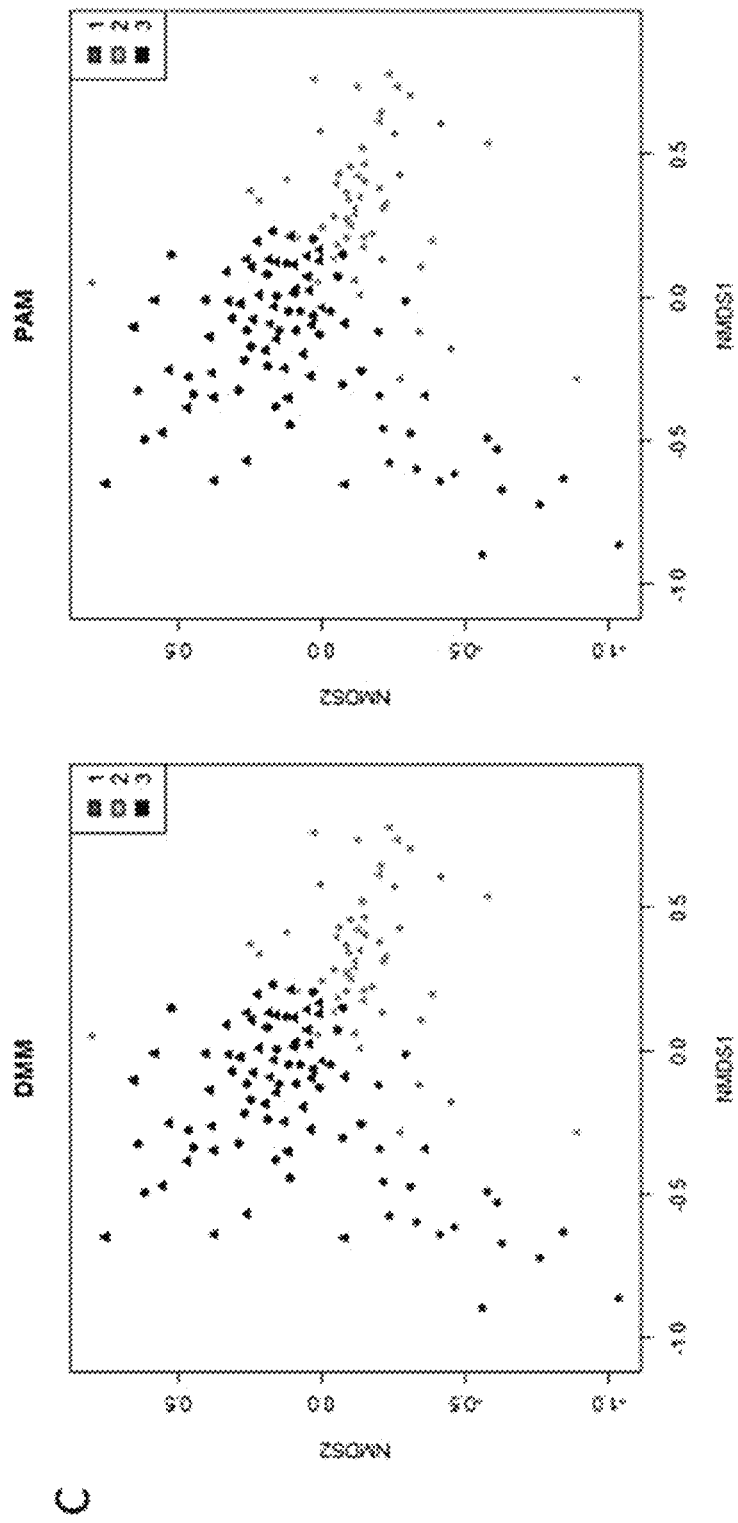
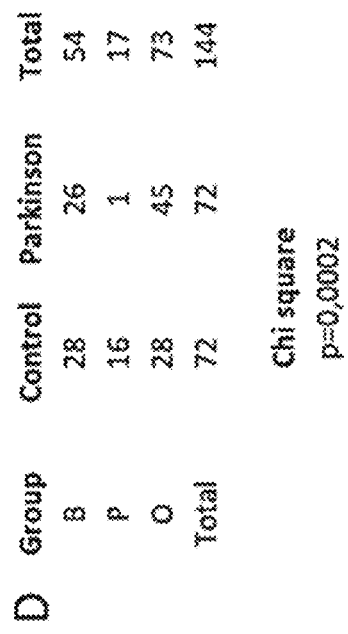
FIGURE 7C
FIGURE 7D

METHOD FOR DIAGNOSTICS, TREATMENT AND PREVENTION OF PARKINSON'S DISEASE

RELATED APPLICATION DATA

This application is a continuation application which claims priority to U.S. patent application Ser. No. 17/116,045, filed on Dec. 9, 2020, which is a divisional application which claims priority to U.S. patent application Ser. No. 15/314,240, filed on Nov. 28, 2016, which is a National Stage Application under 35 U.S.C. 371 of co-pending PCT application PCT/FI2015/050374 designating the United States and filed May 28, 2015; which claims the benefit of FI application 20145492 and filed May 28, 2014 each of which are hereby incorporated by reference in their entireties.

SEQUENCE LISTING

The instant application contains a Sequence Listing which has been submitted electronically in XML format and is hereby incorporated by reference in its entirety. Said XML copy, created on Mar. 27, 2023, is named "2140795USD3" and is 3 KB in size.

FIELD OF THE INVENTION

The present invention relates to the field of medicine and in particular to Parkinson's disease (PD). Specifically the present invention relates to methods and means for early detection of PD. The invention relates also to methods and means for treatment or prophylaxis of PD.

BACKGROUND OF THE INVENTION

Parkinson's disease is the most frequent movement disorder. The prevalence in people above 65 years is approximately 1% and it has a great negative effect on quality of life. The cause of Parkinson's disease (PD) is unknown and there are no disease modifying treatments available. In Parkinson's disease (PD), the cardinal motor symptoms are mainly related to the loss of dopaminergic neurons in the substantia nigra. However, neuropathologic changes are much more widespread involving the autonomic nervous system, olfactory structures, lower brainstem and cerebral cortex. Extranigral pathology is related to a broad spectrum of non-motor symptoms (NMS) that have been increasingly recognized as an important feature of PD. Gastrointestinal dysfunction, in particular constipation, affects up to 80% of PD-patients and may precede the onset of motor symptoms by years (Savica et al. 2009). Idiopathic constipation is one of the strongest risk-factors for PD (Noyce et al. 2012).

It is not known what factors initiate the pathophysiological cascade leading to neurodegeneration in PD, but an environmental factor likely plays a key role in PD pathogenesis probably against a background of genetic vulnerability (Kieburtz et al. 2013). The early involvement of the gastrointestinal tract in PD lends support to the hypothesis that this environmental factor exerts its influences primarily via the gut. However, recent studies have revealed that, changes of the complex equilibrium of the entire microbiome may be related to human disease.

Intestinal microbiota have gained a lot of attention in research in recent years and dysequilibrium of the gut microbiome has been associated with several diseases, including autism, bowel disease and cancer, rheumatoid arthritis, diabetes, and obesity. The gut microbiome in PD has not been previously investigated.

Currently there is no method available for an early diagnostics of PD. Biomarkers for PD, especially for the premotor phase, are urgently needed since future disease modifying therapies should be initiated as early as possible in the disease process to maximize their effect. Moreover, there is no disease modifying treatment available for PD.

BRIEF DESCRIPTION OF THE INVENTION

An object of the present invention is thus to provide methods and means for early detection of PD. A further object is to provide methods and means for treatment or prophylaxis of PD.

The objects of the application are achieved by a method for measuring the probability of a subject developing or having Parkinson's disease (PD), the method comprising
 a. obtaining a sample from a subject;
 b. determining relative abundances of at least Prevotellaceae taxa in the sample; and
 c. determining probability of the subject developing or having PD based on the abundances measured in b,
 wherein a high relative abundance of said taxa indicates a low probability of the subject developing or having PD.

Further the present invention provides a method for determining a motor subtype of a PD patient, wherein method comprises:
 obtaining a sample from a subject;
 determining the abundance of one or multiple of the following taxa: Enterobacteriaceae, *Clostridium* XVIII, *Anaerofilum, Papillibacter, Succiniclasticum, Klebsiella, Escherichia Shigella* and *Paludibacter* in said sample; and determining by statistical methods the motor subtype based on the measured abundances, wherein low relative abundance of the said taxon or taxa indicates a tremor dominant subtype and high relative abundance indicates a non-tremor subtype.

Additionally, the present invention provides a kit for detection and risk assessment of PD.

Further, the present invention provides a method for treatment of patients with PD preferably before the appearance of motor symptoms of PD, or for prophylaxis of PD in subjects with conditions or symptoms indicating an increased risk for PD, the method comprising administering an effective amount of a composition that increases the relative abundance of Prevotellaceae in the intestines to a subject in need of such treatment.

Additionally, the present invention provides a composition increasing abundance of Prevotellaceae in the intestine for use in treatment or prevention of PD.

The preferred embodiments of the invention are disclosed in the dependent claims.

The inventors of the present application surprisingly noticed an association of microbiota, especially gut microbiota and neurodegenerative disease. The inventors found that PD patients did not only have an altered microbiome when compared to matched control subjects, but microbiota were associated also with the motor phenotype of PD. These findings were independent of controlled confounders such as degree of constipation, disease duration, medication, comorbidities, gender, or age.

The present invention provides a novel approach for the diagnostics of PD. The method is rapid, non-invasive and easy to use. The present invention provides a considerable advantage of enabling the individuals having a risk of PD being diagnosed at an early stage preferably before motor symptoms appear e.g. in patients with severe constipation of unknown cause or irritable bowel syndrome. Once diagnosed at an early stage as belonging to the risk group, the onset of PD in the individual can be prevented by modifying the community structure of the gut microbiota. The present invention specifically provides novel means for preventing PD in a subject and also means for slowing the disease process or even stopping it. The combination of the method and the composition of the invention enable development of personalized treatment and possibly personalized dietary guidance. A further advantage of the invention is that the present method to measure the risk of a person to develop PD provides also a new tool for investigation of patients with irritable bowel syndrome (IBS) that currently is a diagnose of exclusion (other possible sources of symptoms are excluded). A considerable fraction of these patients do have premotor PD and the present invention the first test that can be used to identify PD at this stage. IBS symptoms are frequently severe and impairing quality of life (pain, constipation, diarrhea) and treatment is purely symptomatic. Diagnosing PD in these patients using the methods of the present invention opens a way for disease modifying treatment. The same applies to patients with idiopathic constipation.

Still a further advantage of the invention is that selecting donors for fecal transplantation to PD subjects based on high Prevotellaceae abundance ensures effective treatment and is a clear improvement to a transplantation of feces with unknown microbiome structure.

The present invention may improve gut function in PD patients leading to relief of gastrointestinal symptoms including constipation and IBS, improved nutritional status. It may increase levels of thiamine, folate, short chain fatty acids, hydrogen sulfide, and gut hormones like ghrelin in the body of PD patients leading to alleviation of symptoms and slowing of disease progression. *Prevotella* enterotype is associated with high production of these molecules and those have been shown to be decreased in PD and effective in PD treatment.

The present invention may provide a tool for differentiating patients with PD from patients with another disease mimicking PD (such as Progressive supranuclear palsy, Multiple system atrophy, Corticobasal degeneration, vascular parkinsonism, Alzheimer's disease, Essential tremor, Normal pressure hydrocephalus)

The method of the invention improves barrier function of the gut mucosa reducing exposure to bacterial endotoxin, inflammation and oxidative stress in the patient organism leading to better health.

Since microbiota composition is associated with certain medications e.g. COMT-inhibitors, analysis of microbiota in PD patients can be useful to select the optimal medications for a patient, minimizing adverse side effects.

BRIEF DESCRIPTION OF THE DRAWINGS

In the following the invention will be described in greater detail by means of preferred embodiments with reference to the attached drawings, in which.

Figure 3:
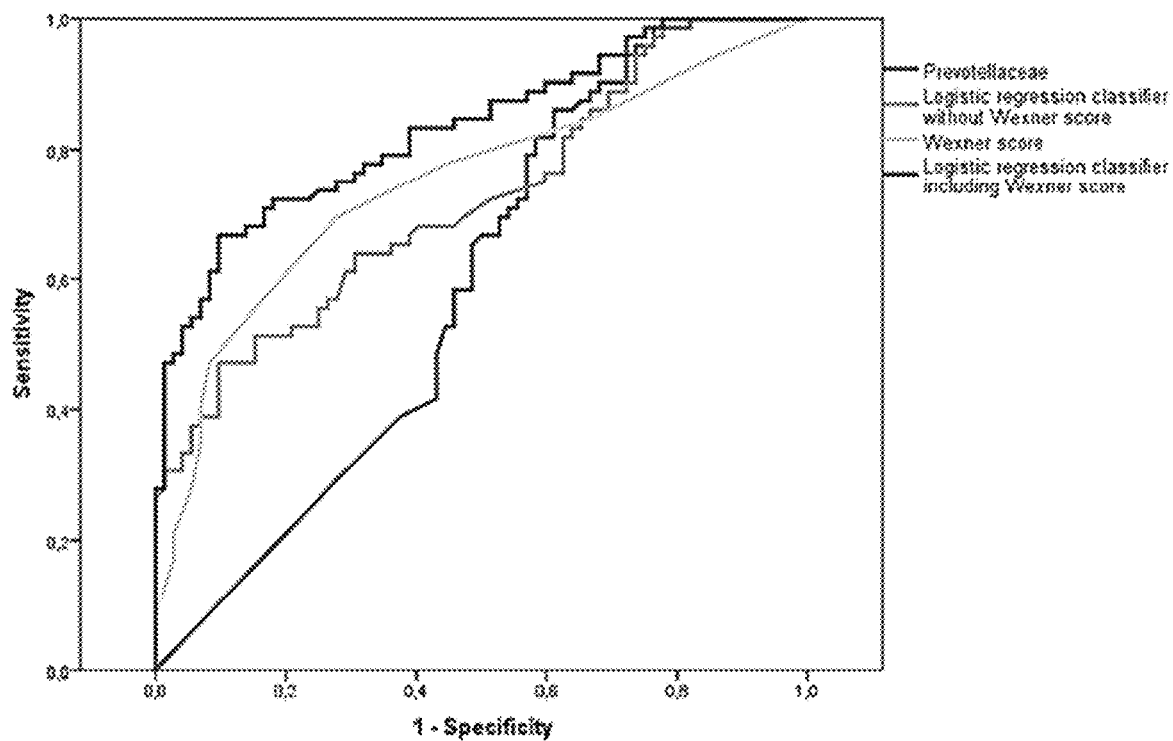

Box plots show the distributions of Prevotellaceae abundance in both study groups. Black horizontal lines indicate the median values and the boxes around them delineate the IQR. Whiskers extend to the highest value within 1.5 IQR of the upper quartile. Circles represent outliers beyond the whisker limit and asterisks represent extreme outliers beyond 3 IQR of the upper quartile. Median [IQR]: Parkinson 0.16% [0.00%-1.66%]; Control: 0.77% [0.00%-18.18%];

FIG. 3 shows ROC curves of discriminators of study group membership

Figure 4:
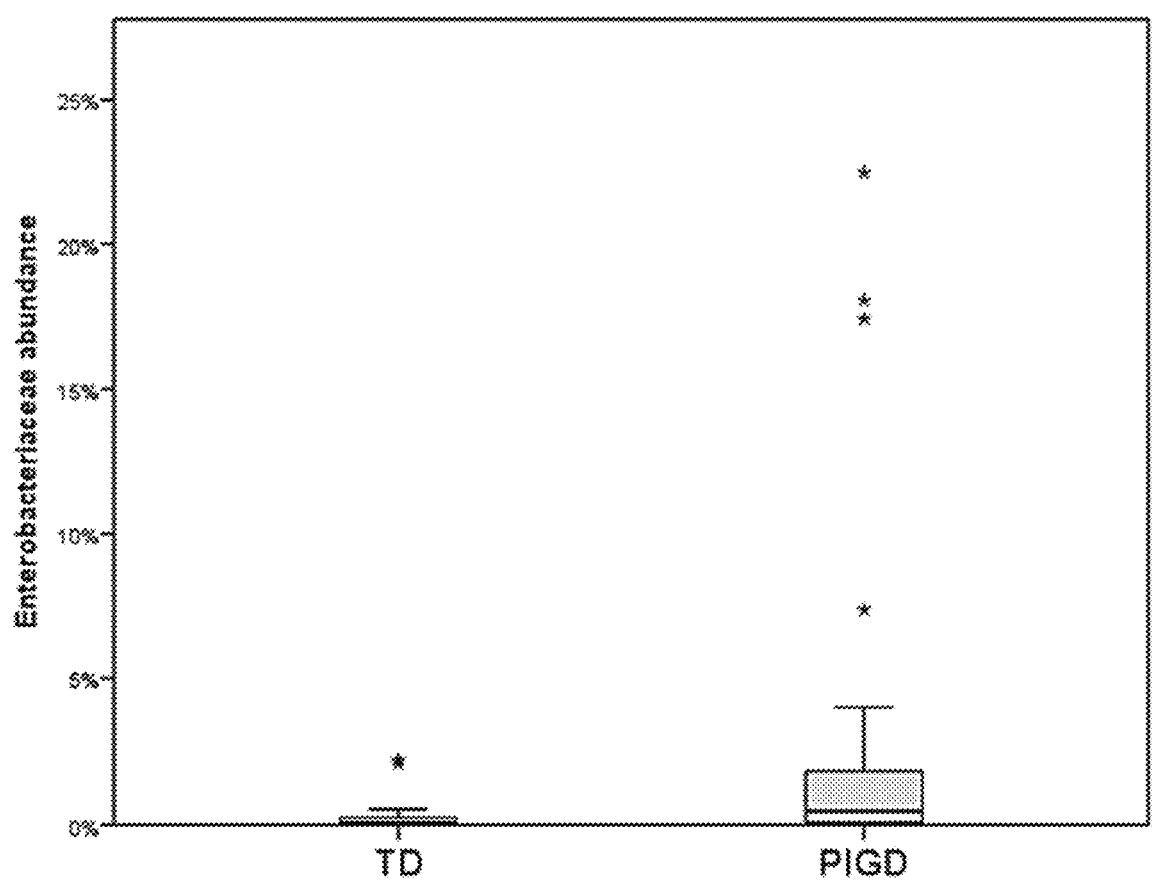

The ROC curve analysis of Prevotellaceae abundance was somewhat hampered by the considerable number of samples in both groups being devoid of this family (AUC=0.591 [95% CI 0.496-0.685], P=0.060). Since samples devoid of Prevotellaceae were equally frequent in PD and control groups, we performed a second ROC curve analysis only including subjects positive for Prevotellaceae (n=103; AUC=0.664 [95% CI 0.556-0.771]; P=0.004; not shown). Logistic regression classifier including abundances of Prevotellaceae, Lactobacillaceae, Bradyrhizobiaceae and Clostridiales Incertae Sedis IV: AUC=0.722 [95% CI 0.641-0.804], P<0.001. Wexner score: 0.747 [95% CI 0.666-0.828], P<0.001. Logistic regression classifier as above, but including also Wexner constipation score: AUC=0.832 [95% CI 0.766-0.897], P<0.001;

FIG. 4 shows distribution of Enterobacteriaceae in phenotypic subgroups of PD

Figure 5:
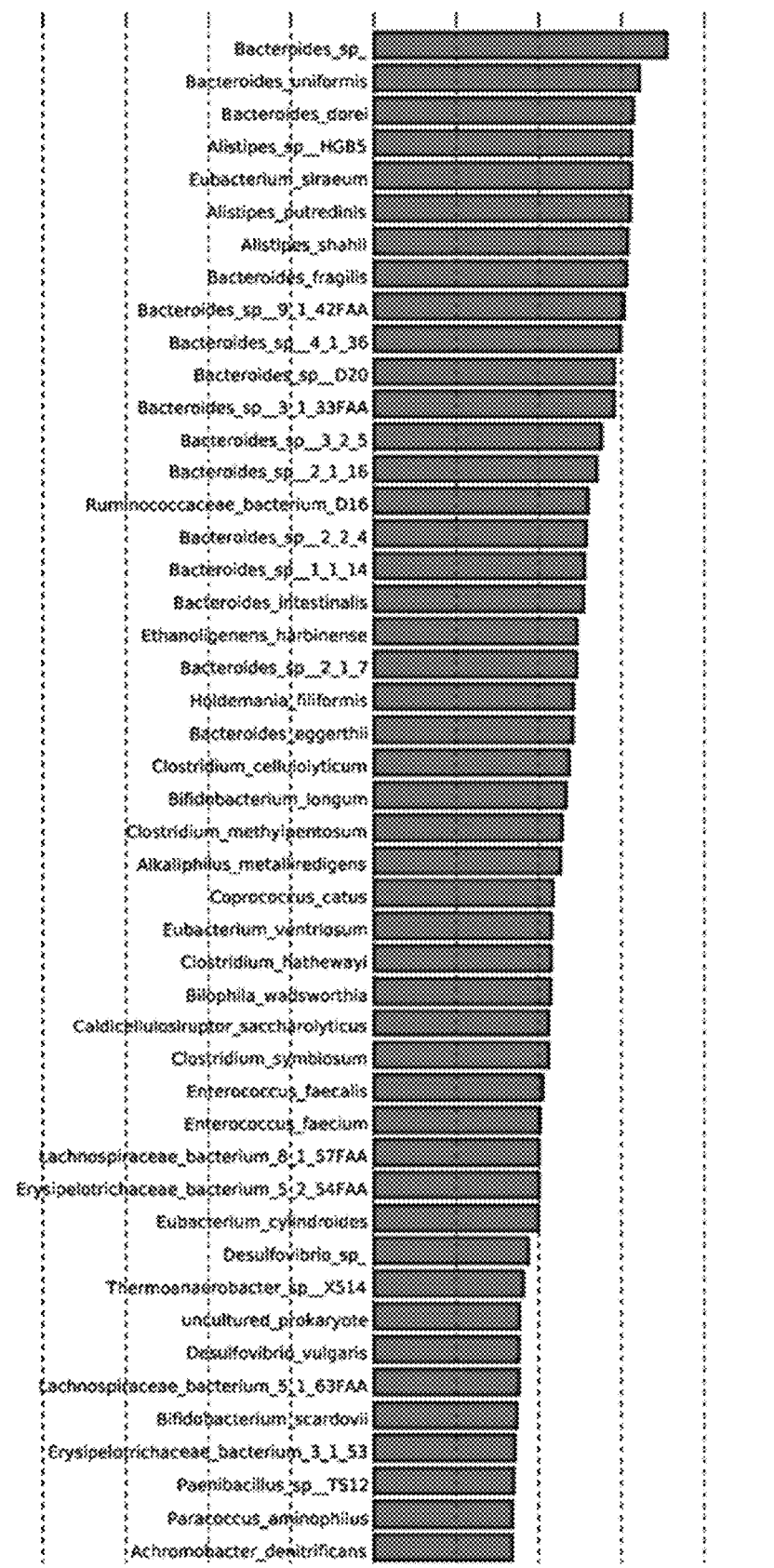
Figure 5:
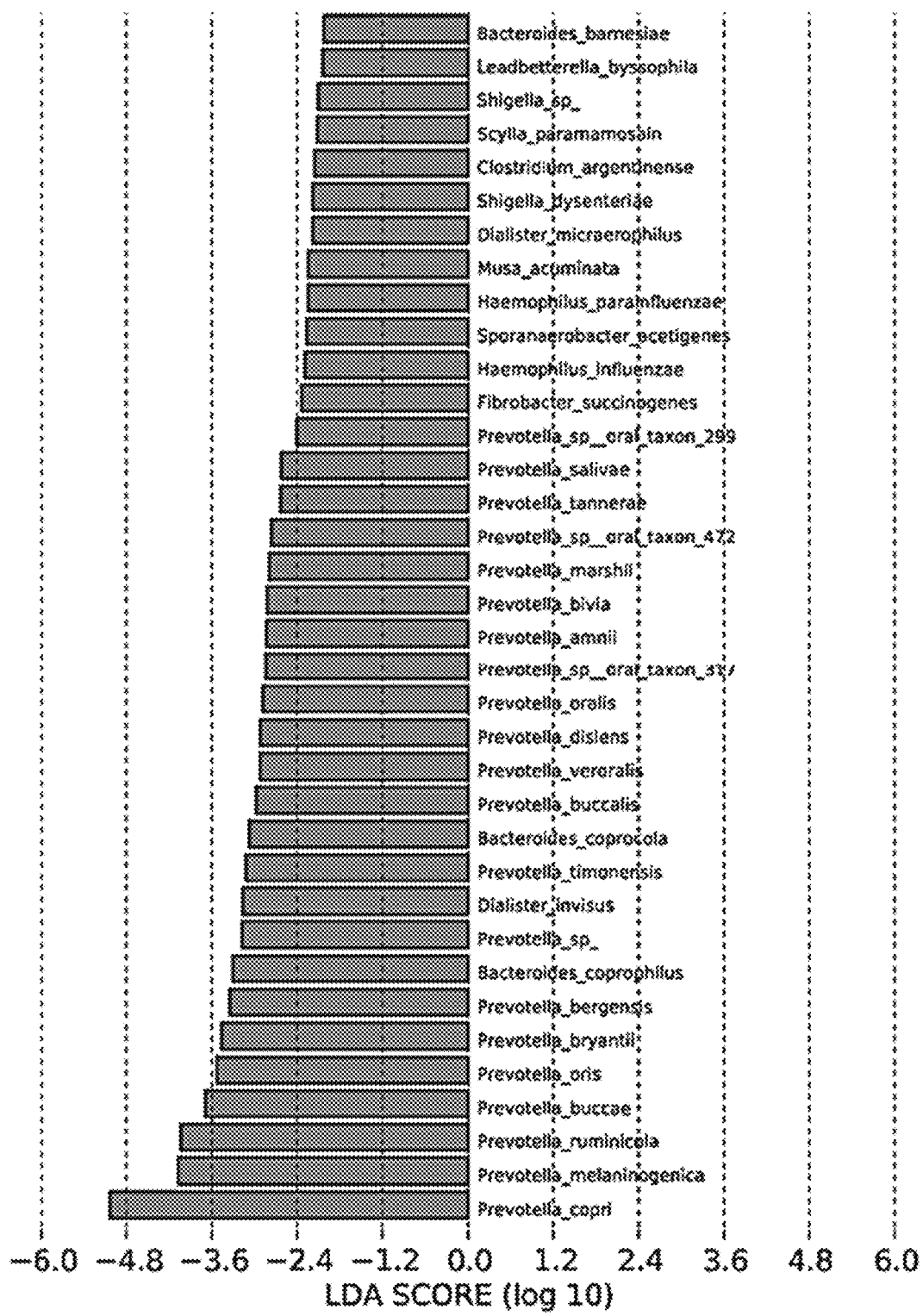

Box plots showing the distributions of Enterobacteriaceae abundances in tremor dominant (TD) and postural instability/gait difficulty (PIGD) phenotypes. Black horizontal lines indicate the median values and the boxes around them delineate the IQR. Whiskers extend to the highest value within 1.5 IQR of the upper quartile. Asterisks represent extreme outliers beyond 3 IQR of the upper quartile. Median [IQR]: TD (0.04 [0.00-0.27]; n=23); PIGD (0.46 [0.07-1.84]; n=40);

FIG. 5 shows microbial taxa that can be used as biomarkers for the diagnosis of PD. We chose 10 PD fecal samples with lowest abundances of Prevotellaceae and highest abundances of Ruminococcaceae. The other 10 were control samples with high abundances of Prevotellaceae. For identification of taxa, DNA from fecal samples was shotgun sequenced using Illumina MiSeq. Sequences equal or above 75 nucleotides were taxonomically identified using MGRast. Biomarkers for PD were selected using the LEfSe method (Segata et al, 2011). The plots show the biomarkers found by LEfSe ranking them accordingly to their effect size and associating them with the class with the highest median. Green columns indicate taxa more abundant in PD patients and red columns indicate taxa more abundant in control subjects.

Figure 6A:
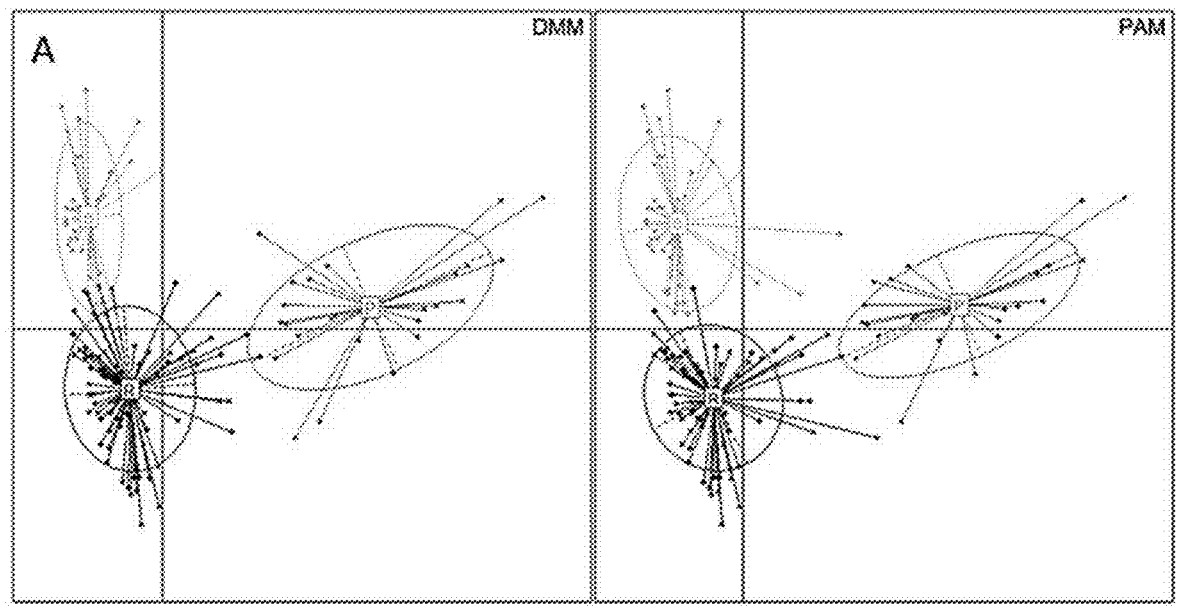
Figure 6B:
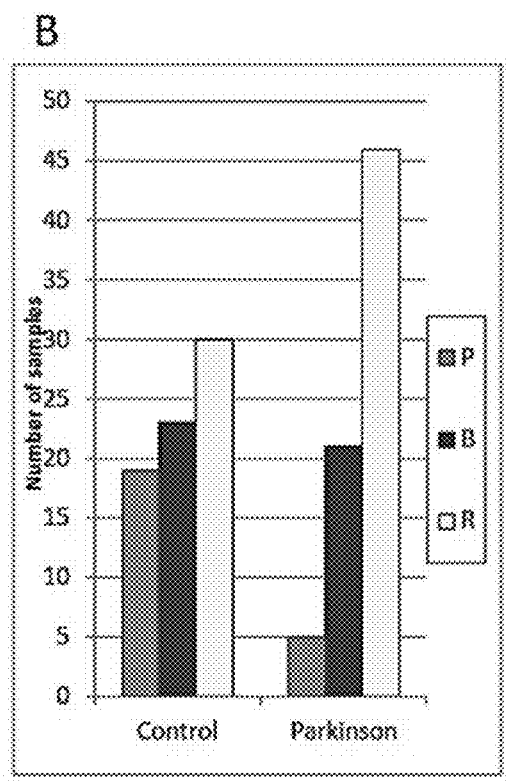
Figures 6C, 6D:
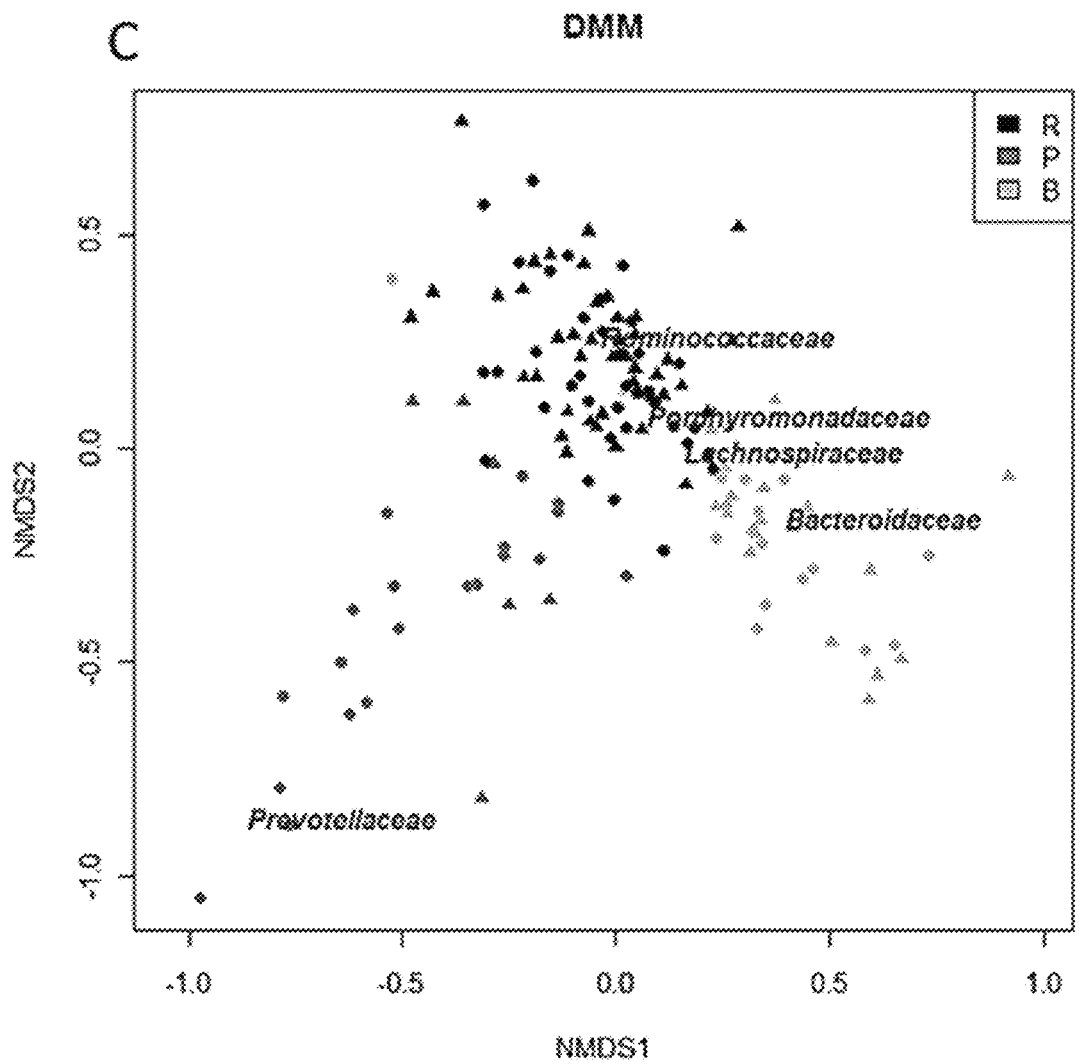
Figure 6E:
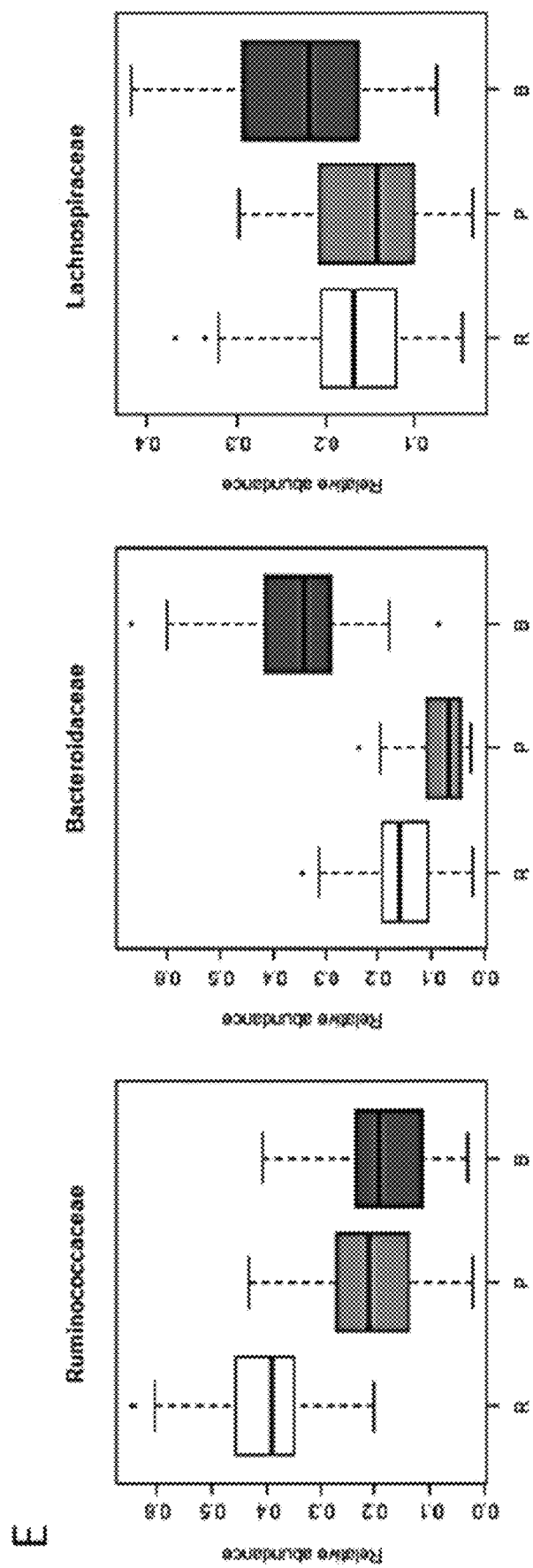
Figure 6E:
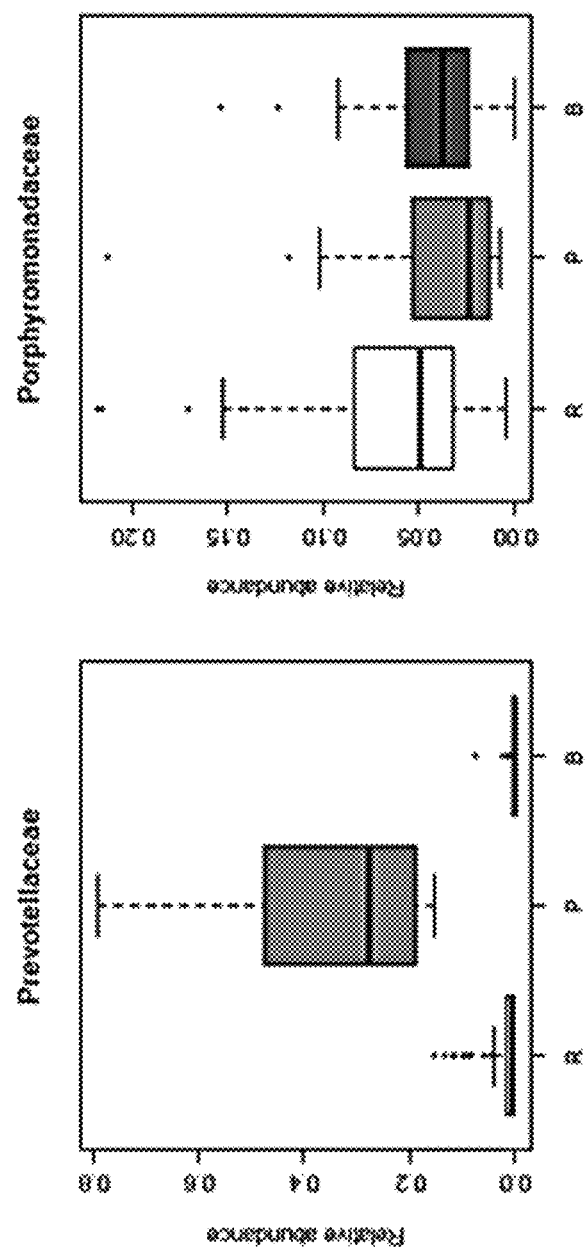
Figure 6F:
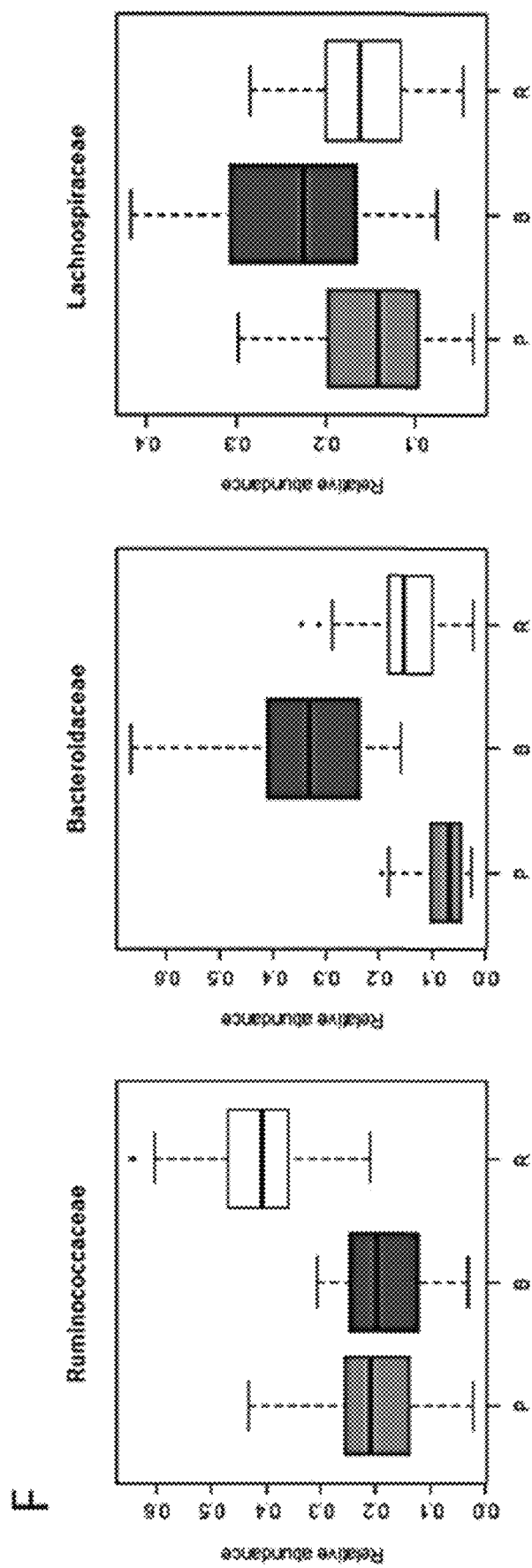
Figure 6F:
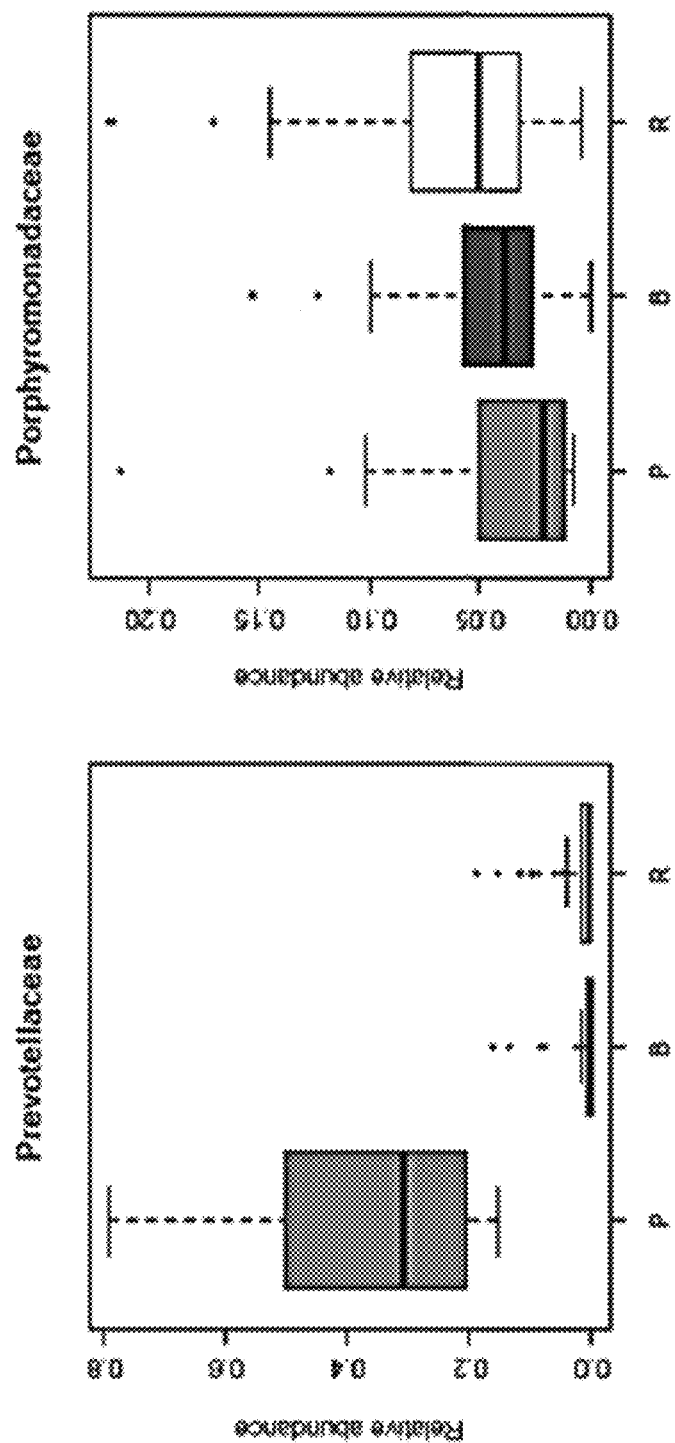

FIGS. 6A-6F show plots and data generated using the partitioning around the medoid (PAM) and Dirichlet multinomial mixture (DMM) methods to classify samples into groups based on similarity of their microbiome community structure on bacterial family level (fecal samples of 72 PD patients and 72 control subjects with microbiome community structure determined as described previously (Arumugam et al. 2011). FIG. 6A: Results of principal component analysis demonstrating that samples are classified into 3 groups (P, R, B). FIGS. 6B and 6D: Only 5 PD subjects, but 19 control subjects were assigned to group P. Chi Square test confirming significant association between study group and classification group. FIG. 6C Non-metric Multidimensional Scaling arranging individual subject samples according to similarity of microbiome community structure. The closer two samples, the more similar the microbiome. Dots=control subjects, Triangles=PD patients. The plot also shows the dominating families. FIGS. 6E and 6F Relative abundance of the five most abundant families in the three groups based on the DMM (E) and PAM (F) methods. Both methods show that the P group shows particularly high abundance of Prevotellaceae, whereas the R group is dominated by Ruminococcaceae and the B group mainly by Bacteroidaceae.

Figure 7A:
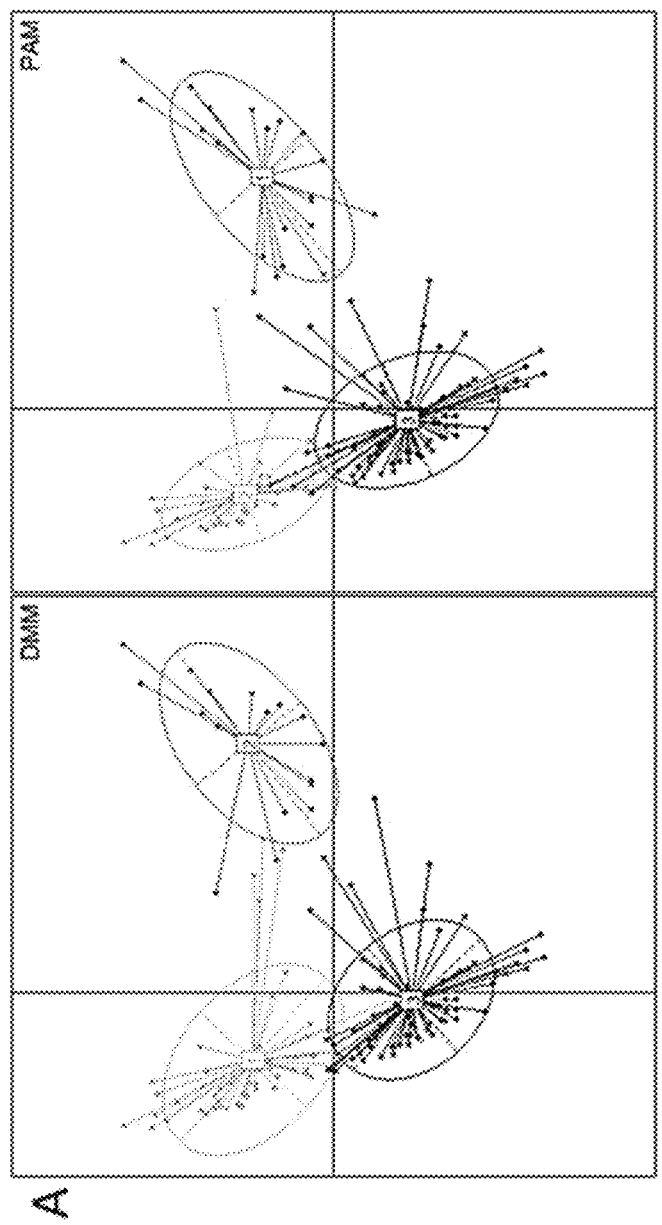
Figure 7B:
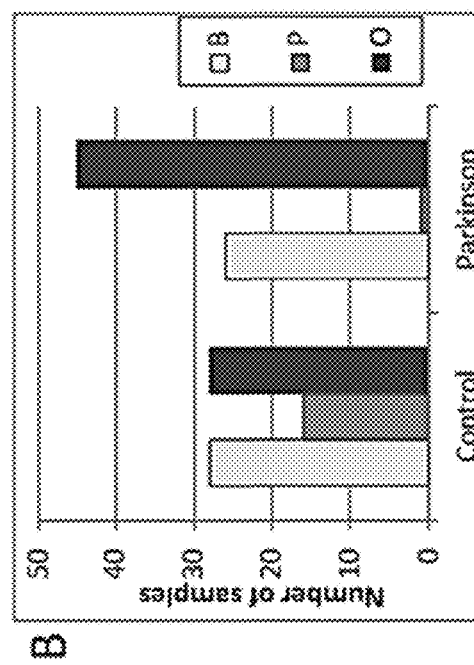
Figure 7E:
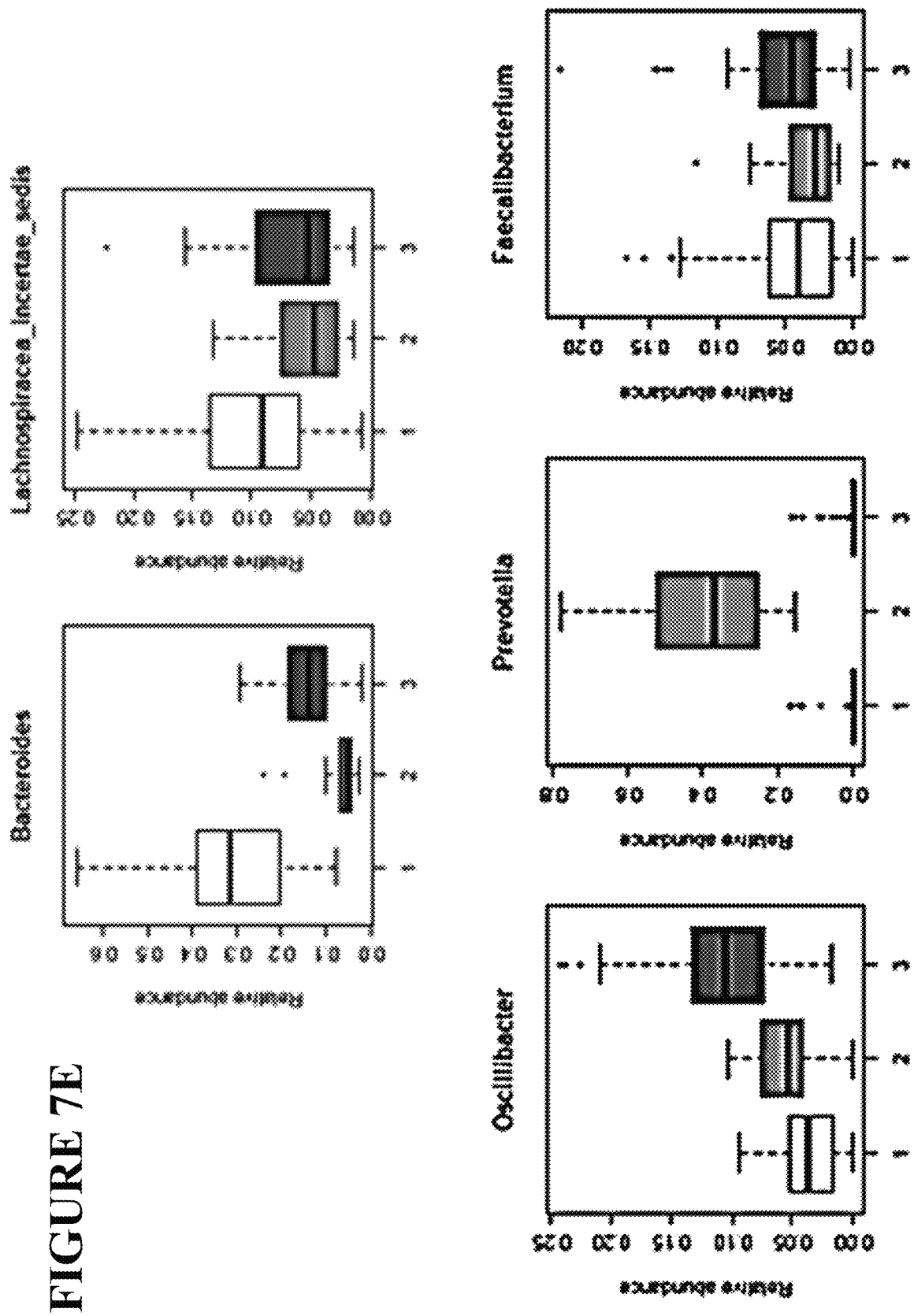
Figure 7E:
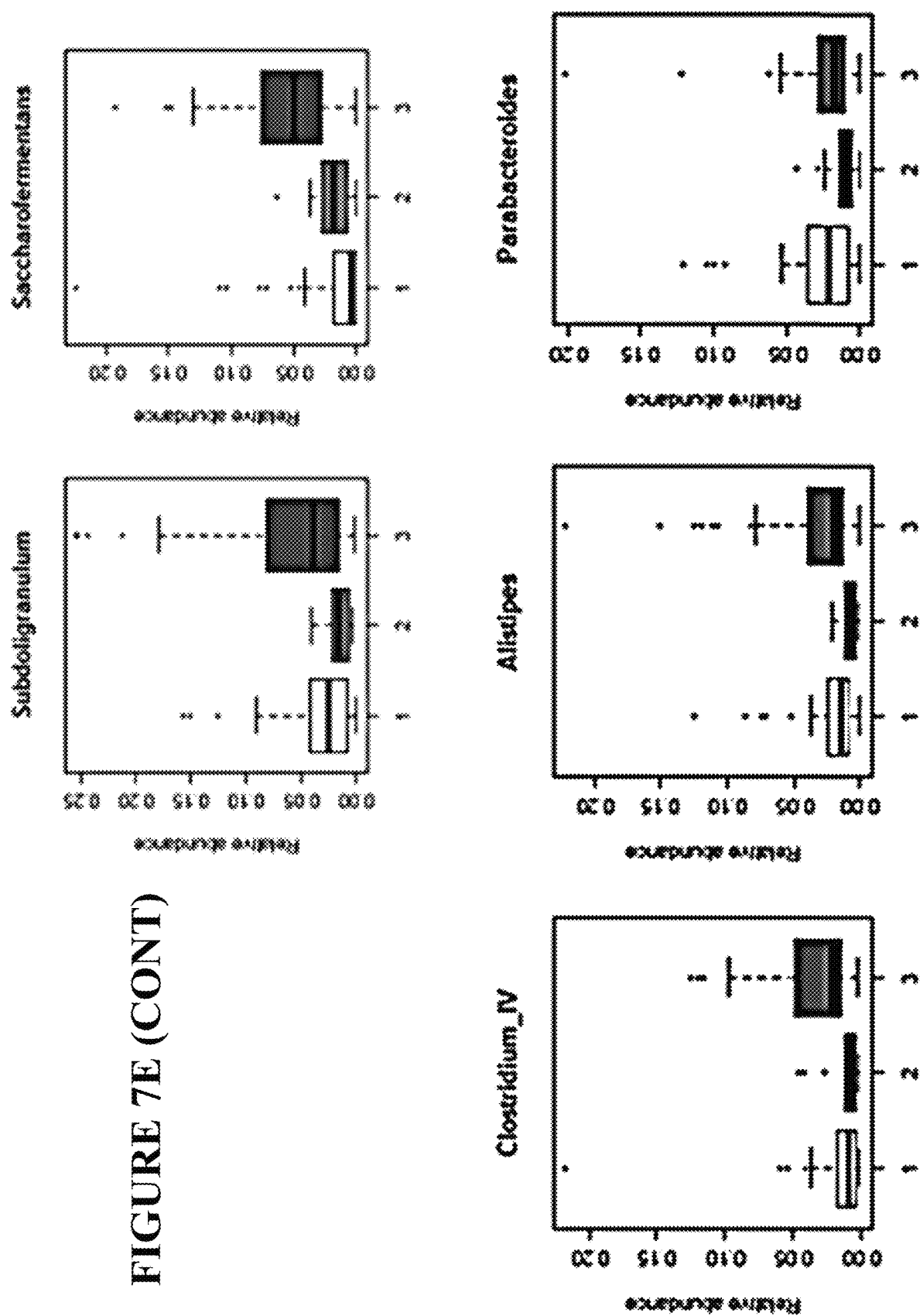
Figure 7F:
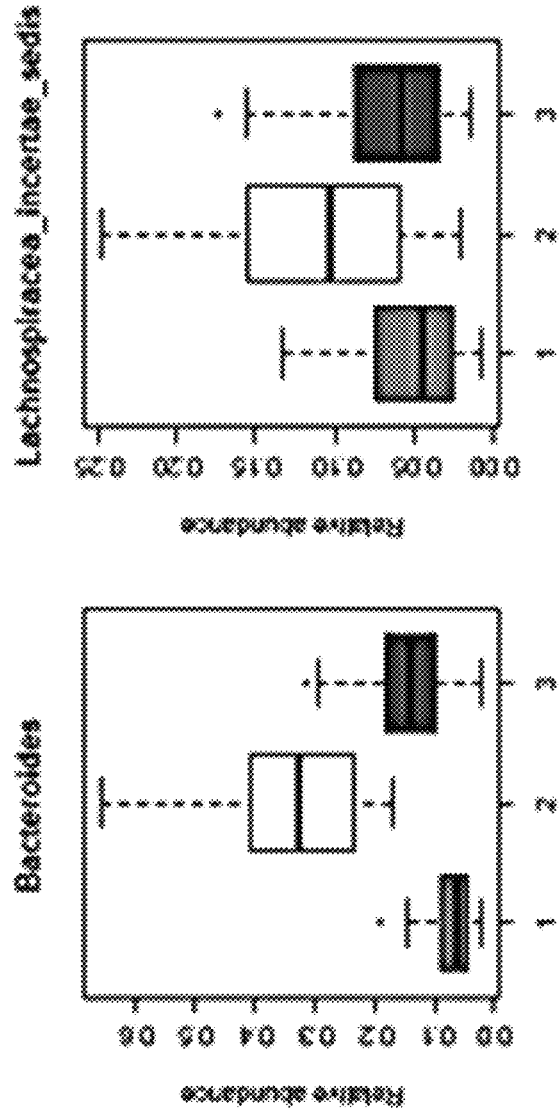
Figure 7F:
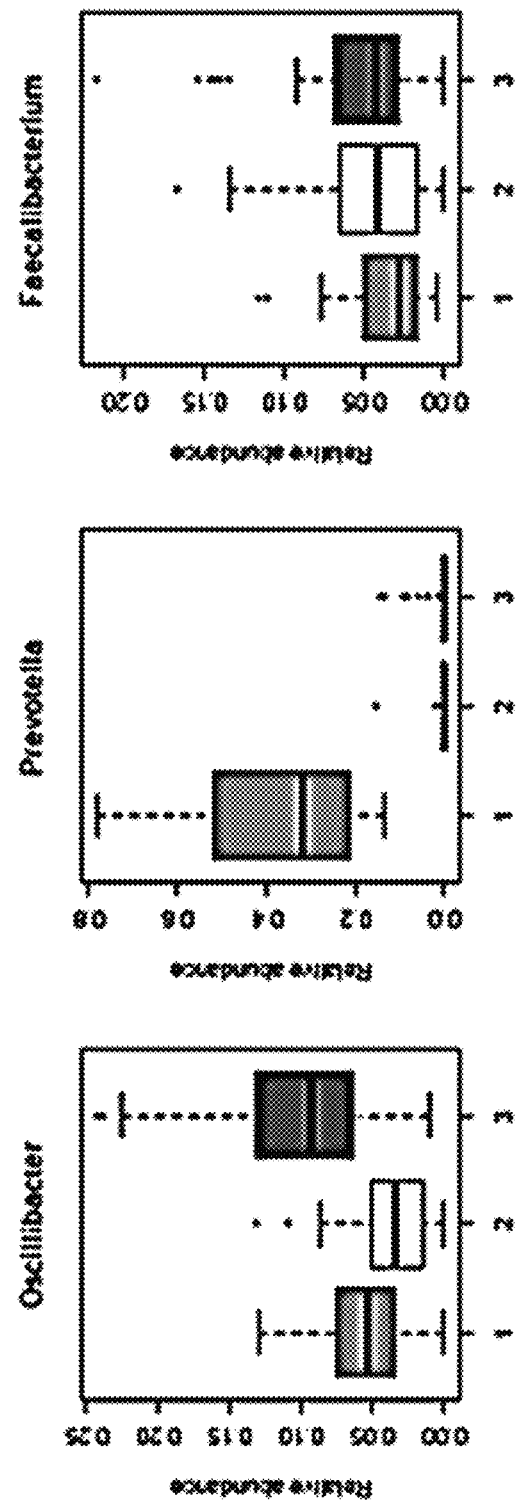
Figure 7F:
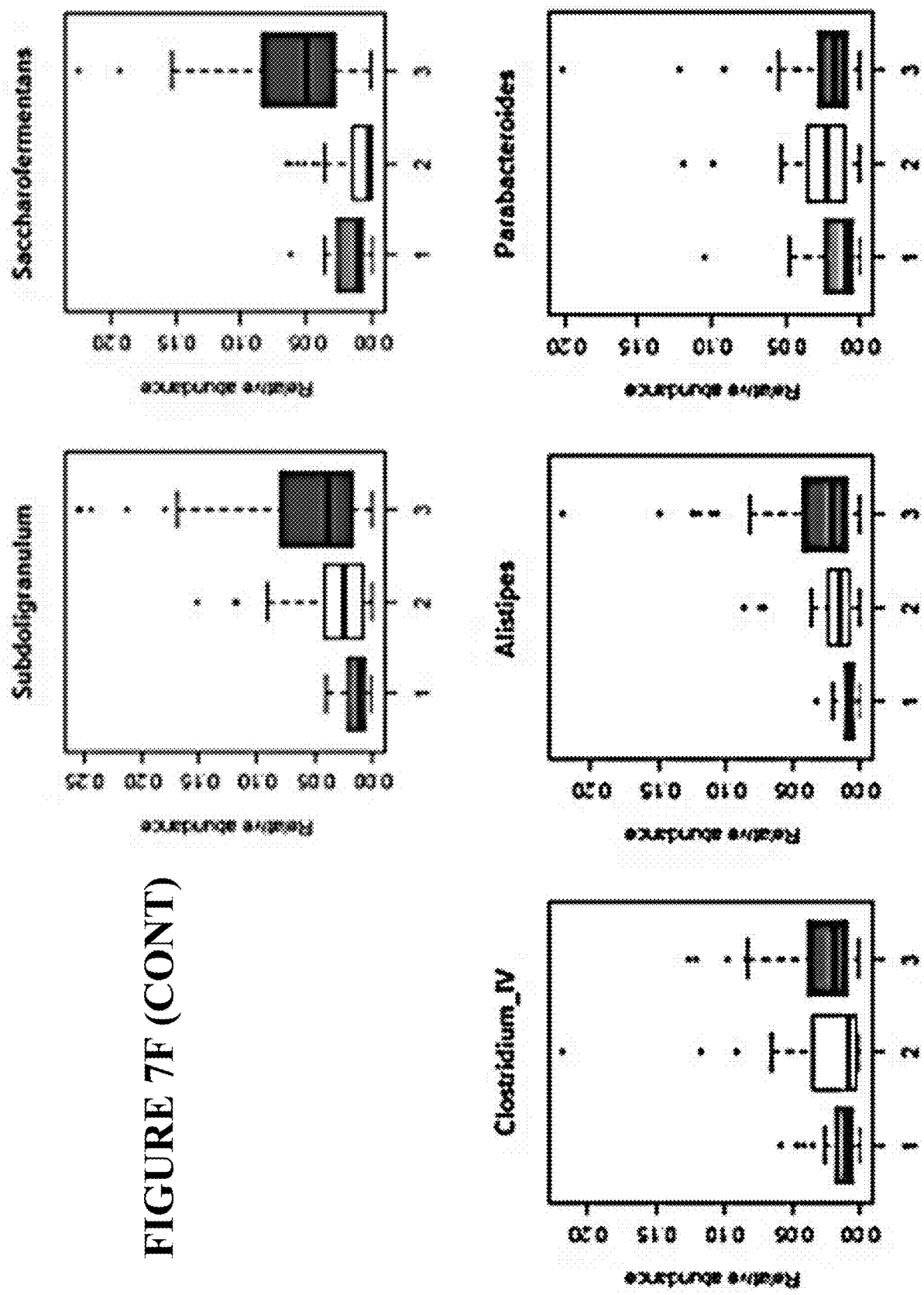

FIGS. 7A-7F show plots and data generated using the same techniques and samples as for FIGS. 6A-6F, but for the bacterial genus level. FIG. 7A: Results of principal component analysis demonstrating that samples are classified into 3 groups. FIGS. 7B and 7D: Only 1 PD subject, but 16 control subjects were assigned to group P (=group 1 from DMM) whereas 45 PD subjects, but only 28 subjects were assigned to group 0 (=group 3 from DMM). Chi Square test confirming significant association between study group and classification group. FIG. 7C Nonmetric Multidimensional Scaling arranging individual subject samples according to similarity of microbiome community structure. The closer two samples, the more similar the microbiome. Dots=control subjects Triangles=PD patients. FIGS. 7E and 7F Relative abundance of the ten most abundant genus in the three groups based on the DMM (E) and PAM (F) methods. The P group (=group 2 in E and group 1 in F) shows particularly high abundance of *Prevotella*, whereas the B group (=group 1 in E and group 2 in F) is dominated by *Bacteroides* and Lachnospiraceae incertae sedis. Group O (=group 3) shows relatively high abundance of *Oscillibacter* and *Saccharofermentans*.

Figure 8:
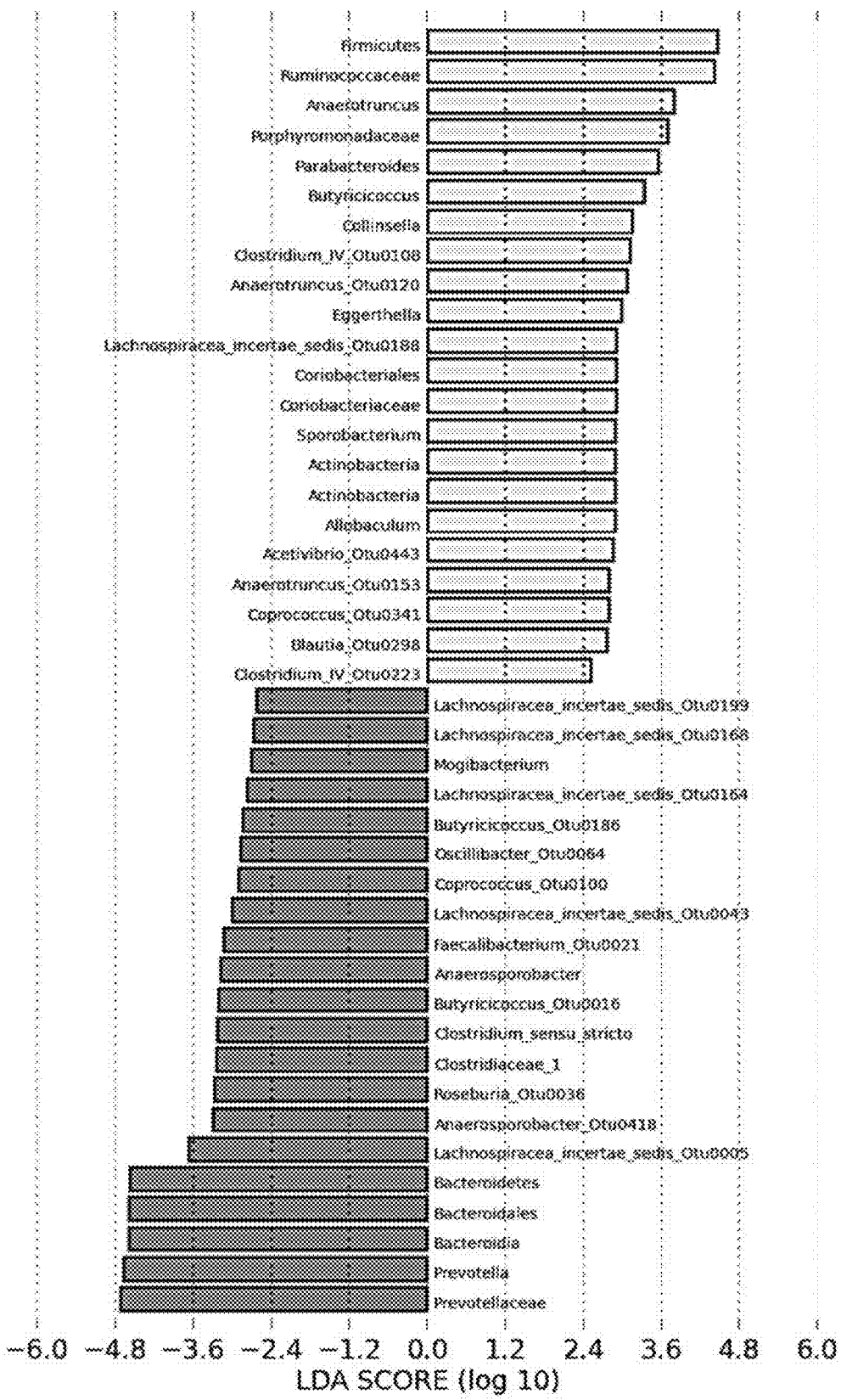

FIG. 8 shows microbial taxa that can be used as biomarkers for the diagnosis of PD based on analysis of 72 PD and 72 control fecal samples. Biomarkers for PD were selected using the LEfSe method. The plots show the biomarkers found by LEfSe ranking them accordingly to their effect size and associating them with the class with the highest median. Light grey columns indicate taxa more abundant in PD patients and dark grey columns indicate taxa more abundant in control subjects.

DETAILED DESCRIPTION OF THE INVENTION

The present invention relates to a method, wherein the probability of a subject developing or having Parkinson's disease (PD) is determined by a method wherein a sample is obtained from a subject; relative abundances of one or more microbial taxa in the sample are measured; and probability of the subject developing or having PD is determined based on the measured relative abundances of one or multiple microbial taxa in the sample.

The present invention concerns generally Parkinsons's disease and also Parkinsons's disease where the definition of PD includes a prodromal and a premotor period of the disorder in which the subject has no motor symptoms. A prodromal period means a period of early symptoms that might indicate the start of a disease before specific symptoms occur. In a pre-motor period typical motor symptoms of PD have not yet developed although neurons in the autonomic nervous system or brain have started to degenerate. Generally, PD is suspected based on the subject having one or more of the following conditions that are associated with PD: family history of PD, family history of tremor, constipation, irritable bowel syndrome, hyposmia, REM-sleep behavior disorder, mood disorder, hyperechogenicity of the substantia nigra on transcranial ultrasound examination.

In the present invention relative abundances of one or more microbial taxa in a sample are measured. A sample is a microbial sample taken from an individual. Preferably it is a gut microbiota sample obtained from lower gastrointestinal tract, more preferably it is e.g. feces sample. The sample may also be an oral or nasal mucosal swab sample.

Gut flora or, more appropriately, gut microbiota, consists of a complex community of microorganism species that live in the digestive tracts of human and animals and is the largest reservoir of microorganisms mutual to humans. In this context gut is synonymous with intestinal, and flora with microbiota and microflora. The gut microbiome refers to the genomes of the gut microbiota, but is also used synonymously with microbiota and microflora.

In the present invention the probability of the subject developing or having PD is determined based on the measured relative abundances of one or multiple microbial taxa in the sample. The high relative abundance is defined as being higher as a reference value, which is a predefined threshold value, and vice versa. Relative abundance means the abundance of a microbial taxon relative to the sum of the abundances of all taxa detected in a sample.

A reference sample is a sample from an individual not having PD and having a low risk of developing PD. Indicators of low risk are e.g. no strong family history of PD, no strong family history of tremor, no constipation, no irritable bowel syndrome, no hyposmia, no REM-sleep behaviour disorder, no mood disorder. In the method of the invention taxa abundances in reference samples including samples from PD patients can be used to generate a logistic regression model, wherein the probability of developing or having PD is modelled as a function of taxa abundances. The value of a logistic regression classifier is calculated based on said logistic regression model and the values of the subject. The value of said logistic regression classifier is then used to determine the probability of the subject developing or having PD.

The relative abundance of the microbial taxa can be measured using techniques based on DNA sequencing, quantitative PCR, DNA microarray, by using test beds utilizing arrays or other suitable platforms including microfluidistic solutions, techniques based on droplet PCR, or any other suitable method wherein the abundance of taxa is expressed as read count, percentage, cell count, or value expressing intensity of any other suitable signal.

A microbial taxon as used herein refers to a taxonomic unit, whether named or not: i.e. a population, or group of populations of organisms which are usually inferred to be phylogenetically related and which have characters in common which differentiate the unit (e.g. a genus, a family) from other such units. A taxon encompasses all included taxa of lower rank and individual organisms. The term as used herein furthermore includes termed species-level phylotypes or operational taxonomic units that are identified only by their complete 16S rRNA sequence and usually defined as sharing 97% or less sequence identity with other entries in the ribosomal databases. In the present invention the measurement of relative abundances of microbial taxa may include all taxa that can be identified in a sample.

In the method of the invention the microbial taxa is preferably Prevotellaceae, and more preferably *Prevotella*. According to one embodiment of the invention the taxon is one or more of the following: *Prevotella amnii, Prevotella bergensis, Prevotella bivia, Prevotella bryantii, Prevotella buccae, Prevotella buccalis, Prevotella copri, Prevotella disiens, Prevotella marshii, Prevotella melaninogenica, Prevotella oralis, Prevotella oris, Prevotella ruminicola, Prevotella salivae, Prevotella* sp oral taxon 299, *Prevotella* sp oral taxon 317, *Prevotella* sp oral taxon 472, *Prevotella tannerae, Prevotella timonensis* and *Prevotella veroralis*.

The basic idea behind the present invention is the finding of the reduced abundance of Prevotellaceae in PD patients. According to the present study, a person with a relative abundance of Prevotellaceae of more than 6.5% is very unlikely to have PD (86.1% sensitivity). In other words, high relative abundance of Prevotellaceae indicates a low probability of the subject developing or having PD.

*Prevotella* is a genus of Gram-negative bacteria. It is a commensal microbe in the human large intestine and has the ability to degrade a broad spectrum of plant polysaccharides. It not only plays a key role in digesting carbohydrate-rich food and degrading of mucin glycoproteins in the mucosal layer of the gut, but may also interact with the immune system. *Prevotella* is the main contributor of one of the recently suggested gut microbiome enterotypes (Arumugam et al. 2011) in addition to *Bacteroides*, and Ruminococcus. The composition of the gut microbiome of an individual is established in early childhood and the enterotype of an individual is thereafter very stable. Therefore the present invention measuring *Prevotella*, *Bacteroides*, and Ruminococcaceae abundances as determinants of the enterotype can also be used to determine the risk of a subject for future development of PD.

In addition to Prevotellaceae, also the abundances of Lactobacillaceae, Verrucomicrobiaceae, Bradyrhizobiaceae, and Clostridiales Incertae Sedis IV were independently associated with PD in the studies of the present invention. Thus, in one aspect of the invention one or more of the following taxa may be included in the measurement: Lactobacillaceae, Verrucomicrobiaceae, Bradyrhizobiaceae, Clostridiales Incertae Sedis IV and Ruminococcaceae.

In one embodiment of the invention low relative abundance of Prevotellaceae and high relative abundances of Lactobacillaceae, Verrucomicrobiaceae, Bradyrhizobiaceae, Clostridiales Incertae Sedis IV and/or Ruminococcaceae indicates a high probability of the subject developing or having PD.

According to another embodiment one or more of the following taxa are included in the determination in addition to *Prevotella*: Sutterella, Saccharofermentans, Mahella, Lactobacillus, Phaeovibrio, Agromonas, and/or Anaerotruncus. In addition to low relative abundance of *Prevotella* low relative abundance of the taxon Sutterella and high relative abundance of the taxa Saccharofermentans, Mahella, Lactobacillus, Phaeovibrio, Agromonas, and/or Anaerotruncus indicates a high probability of the subject developing or having PD.

According to another embodiment one or more of the following taxa are included in the determination in addition to Prevotellaceae and *Prevotella*: Bacteroidia, Clostridiaceae, *Clostridium* sensu stricto, *Faecalibacterium*, *Mogibacterium*, *Oscillibacter*, *Prevotella*, Prevotellaceae, *Roseburia*, *Acetivibrio*, Actinobacteria, *Allobaculum*, *Anaerotruncus*, *Blautia*, *Butyricicoccus*, *Clostridium* IV, *Collinsella*, Coriobacteriaceae, Coriobacteriales, *Eggerthella*, Firmicutes, *Parabacteroides*, Porphyromonadaceae, Ruminococcaceae, *Sporobacterium*. In addition to low relative abundance of *Prevotella* and/or Prevotellaceae low relative abundance of the taxa Bacteroidia, Clostridiaceae, *Clostridium* sensu stricto, *Faecalibacterium*, *Mogibacterium*, *Oscillibacter*, and/or *Roseburia* and high relative abundance of the taxa *Acetivibrio*, Actinobacteria, *Allobaculum*, *Anaerotruncus*, *Blautia*, *Butyricicoccus*, *Clostridium* IV, *Collinsella*, Coriobacteriaceae, Coriobacteriales, *Eggerthella*, Firmicutes, *Parabacteroides*, Porphyromonadaceae, Ruminococcaceae, and/or *Sporobacterium* indicates a high probability of the subject developing or having PD.

According to one embodiment of the invention in addition to the low relative abundance of *Prevotella* and the taxa from one or more of the further bacterial species, which may be selected from the group of *Bacteroides barnesiae*, *Bacteroides coprocola*, *Bacteroides coprophilus*, *Clostridium argentinense*, *Dialister invisus*, *Dialister micraerophilus*, *Fibrobacter succinogenes*, *Haemophilus influenzae*, *Haemophilus parainfluenzae*, *Leadbetterella byssophila*, Shigelladysenteriae, *Shigella* and Sporanaerobacteracetigenes, and the high relative abundance of one or more of the taxa, which may be selected from the following group: *Achromobacter denitrificans*, *Alistipes putredinis*, *Alistipes shahii*, *Alistipes* sp HGBS, *Alkaliphilus metalliredigens*, *Bacteroides dorei*, *Bacteroides eggerthii*, *Bacteroides fragilis*, *Bacteroides intestinalis*, *Bacteroides*, *Bacteroides* sp 1 1 14, *Bacteroides* sp 2 1 16, *Bacteroides* sp 2 1 7, *Bacteroides* sp 2 2 4, *Bacteroides* sp 3 1 33FAA, *Bacteroides* sp 3 2 5, *Bacteroides* sp 4 1 36, *Bacteroides* sp 9 1 42FAA, *Bacteroides* sp D20, *Bacteroides uniformis*, *Bifidobacterium longum*, *Bifidobacterium scardovii*, *Bilophila wadsworthia*, *Caldicellulosiruptor saccharolyticus*, *Clostridium cellulolyticum*, *Clostridium hathewayi*, *Clostridium methylpentosum*, *Clostridium symbiosum*, *Coprococcus catus*, *Desulfovibrio*, *Desulfovibrio vulgaris*, *Enterococcus faecalis*, *Enterococcus faecium*, Erysipelotrichaceae bacterium 3 1 53, Erysipelotrichaceae bacterium 5 2 54FAA, *Ethanoligenens harbinense*, *Eubacterium cylindroides*, *Eubacterium siraeum*, *Eubacterium ventriosum*, *Holdemania filiformis*, Lachnospiraceae bacterium 5 1 63FAA, Lachnospiraceae bacterium 8 1 57FAA, *Paenibacillus* sp TS12, *Paracoccus aminophilus*, Ruminococcaceae bacterium D16, *Thermoanaerobacter* sp X514 indicates a high probability of the subject developing or having PD.

The method of the present invention may include a quantitative measurement of constipation, wherein values indicating constipation indicate a high probability of the subject developing or having PD. The constipation may be measured e.g. by using a questionnaire or an objective assessment of colonic transit time.

In the present invention clinical measures of patient symptoms that may include, but are not restricted to quantitative measurements of constipation, may be included in the logistic regression model. Also information on the presence of PD risk alleles in the genome of the subject may be included in the model.

Specifically, in the method of the present invention taxa abundances from reference samples including samples from PD patients and healthy controls and abundances from the sample of the subject are subjected to a statistical classification method such as, but not restricted to "partitioning around the medoid" and "Dirichlet multinomial mixture", that assigns samples into groups based on their taxonomic composition (Arumugam et al., 2011). If the method from a statistical classification assigns the subject's sample to a group containing few PD samples, the probability of the subject developing or having PD is determined to be low and vice versa. Also if the method from a statistical classification assigns the subject's sample to a group where the samples have higher abundances of one or more of the taxa Prevotellaceae or *Prevotella* as compared to the other groups the probability of the subject developing or having PD is determined to be low.

PD is a clinically heterogenic disorder and it has been suggested that different pathophysiologic mechanisms underlie the observed differences in expression of tremor and non-tremor symptoms between patients. In comparison to tremor dominant (TD) patients, patients with a non-TD phenotype progress faster, have a worse prognosis, and show more severe alpha-synuclein pathology in the colonic enteric nervous system.

The present invention relates also to a method for determining a clinical subtype of a PD patient, especially a motor subtype The method comprises obtaining a sample from a subject; determining the abundance of one or multiple of the following taxa: Enterobacteriaceae, *Clostridium* XVIII, *Anaerofilum, Papillibacter, Succiniclasticum, Klebsiella, Escherichia/Shigella* and *Paludibacter* in said sample; and by using statistical methods determining a motor subtype based on the measured abundances, wherein low relative abundance of the said taxon or taxa indicates a tremor dominant subtype and high relative abundance indicates a non-tremor subtype. The determination of clinical subtypes can be a useful tool to improve research methods and thus find a cure or better treatments, or help to counsel patients or direct existing therapies.

In one aspect the present invention relates to a kit for use in a method of the invention i.e for detection and risk assessment of PD, the comprising means for determining alterations in the microbiota, especially gut microbiota. The kit comprises reagents and means for determining the abundance of one or more of the taxa mentioned in claims of the present invention in a sample.

The present invention relates further to a composition comprising a gut microbiome altering agent that, when administered to an individual, increases the abundance of Prevotellaceae or supports growth of these taxa in the intestine. The composition may comprise live or killed microbes and optionally a pharmaceutically acceptable carrier. Preferably the microbes are from the taxon Prevotellaceae. A composition may also be such that when administered to an individual, it decreases the abundance of one or more of the taxa Lactobacillaceae, Verrucomicrobiaceae, Bradyrhizobiaceae, Clostridiales Incertae Sedis IV, Ruminococcaceae, Lachnospiraceae, Enterobacteriaceae, Bacteroidaceae, *Alistipes, Coprococcus, Anaerotruncus*, Porphyromonadaceae, *Parabacteroides, Butyricicoccus, Collinsella, Eggerthella*, Coriobacteriaceae, *Sporobacterium*, Actinobacteria, *Blautia, Enterococcus, Acetivibrio, Allobaculum Agromonas*, Firmicutes, *Mahella, Phaeovibrio*, Porphyromonadaceae, *Oscillibacter*, and/or *Saccharofermentans* in the intestine.

The composition of the invention may be in the form of a food composition, pharmaceutical composition, nutraceutical, supplement or an anaerobical microbiota culture. It may include probiotics and other micro-organisms, prebiotics, antibiotics, growth factors, bacteriophages etc. The composition may be administered mixed in food or drink, for example, or separately in the form of a tablets, capsules, microcapsules, powders, solutions, pastes, etc. Food composition may be any kind of food (functional, conventional and novel), food supplement, formula for nutritional purposes, or nutraceutical and it may contain any suitable additives and excipients. The effect of the bacterial supplementation may be enhanced by adding prebiotics such as fibre or oligosaccharides to the composition. The composition may also be a prebiotic and optionally contain a pharmaceutically acceptable carrier. The composition may contain live microbes of the taxon Prevotellaceae and a prebioticial agent or compound supporting growth of these taxa and optionally a pharmaceutically acceptable carrier. Generally composition of gut microbiome can be changed by following a long-term diet.

The present invention relates further to a method for treatment or prevention of PD in an individual by administering said individual a composition comprising a gut microbiome altering agent that, when administered to an individual, increases the abundance of Prevotellaceae in the intestine. The composition to be administered may be the composition of the present invention as disclosed above. The composition may also be a stool transplant. The administration of a gut microbiome altering agent can be done e.g via a bacterial composition given orally, via a nasogastric tube, as a suppository, or by fecal microbiota transplantation. Fecal microbiota transplantation (FMT) or a stool transplant is the process of transplantation of fecal bacteria from a healthy individual into a recipient. It involves restoration of the colonic flora by introducing healthy bacterial flora through infusion of stool, e.g. by enema.

When (FMT) or a stool transplant is used the feces donor is preferably previously selected according to the present invention based on a high abundance of Prevotellaceae and/or low abundance of one or more of the taxa Enterobacteriaceae, Lactobacillaceae, Ruminococcaceae, Bacteroidaceae, Lachnospiraceae, Verrucomicrobiaceae, Bradyrhizobiaceae, Clostridiales Incertae Sedis IV, *Alistipes, Coprococcus, Anaerotruncus*, Porphyromonadaceae, *Parabacteroides, Butyricicoccus, Collinsella, Eggerthella*, Coriobacteriaceae, *Sporobacterium*, Actinobacteria, *Blautia, Enterococcus, Acetivibrio, Allobaculum Agromonas*, Firmicutes, *Mahella, Phaeovibrio*, Porphyromonadaceae, *Oscillibacter*, and/or *Saccharofermentans* in feces. It is also preferred that the donor feces is previously selected based on method of the present invention showing that the donor does not have PD and has a low risk of developing PD.

Preferably the treatment or prevention of PD in an individual is initiated before the diagnosis of PD based on results of the microbial analysis of the present invention. The goal of the treatment is to slow the disease process or to even stop it, or even prevent PD. The term "treatment" may refer to both therapeutic treatment and prophylactic treatment or preventative measures, wherein the goal of the treatment is to slow the disease process or even stop it, or prevent PD.

It will be obvious to a person skilled in the art that, as the technology advances, the inventive concept can be implemented in various ways. The invention and its embodiments are not limited to the examples described below, but may vary within the scope of the claims.

Examples

The study was approved by the ethics committee of the Hospital District of Helsinki and Uusimaa and all participants gave informed consent. The study was registered at clinicaltrials.gov (NCT01536769).

Study Subjects

This case-control study compared patients with a diagnosis of PD according to the Queen Square Brain Bank criteria with gender- and age-matched (±five years) control subjects without any signs of parkinsonism or potential premotor symptoms. The chance of recruiting patients with monogenic parkinsonism was minimized by restricting the age of motor-symptom onset to above 50 years and by excluding subjects with more than one relative or one first-degree relative with PD. From the control group subjects with symptoms associated with premotor PD such as hyposmia, REM sleep behaviour disorder (RBD), and accumulation of other NMS were excluded. Further exclusion criteria covered a broad range of conditions and medications that could independently affect the fecal microbiome.

Subjects were recruited from in- and outpatient departments of the participating hospitals as well as via referrals from cooperating neurologists. We also accepted referrals via participants and invited subjects via announcements in patient journals and meetings. Between November 2011 and December 2012, 277 subjects were screened for the study. Of these, 152 (76 patients, 76 controls) were included. All patients were under regular follow-up by a neurologist who was confident in the diagnosis. Patient records were reviewed if available. Due to sample processing 72 patients and 72 controls were included in the final analysis.

Clinical Data Parkinsonian symptoms were measured using the Unified Parkinson's Disease Rating Scale (UPDRS) and the modified Hoehn & Yahr scale (H&Y). The PD patients were classified into postural instability and gait difficulty (PIGD), tremor dominant (TD), and mixed phenotypes (MX) as described by Jankovic et al 1990. In addition, an akinetic-rigid symptom score was calculated as described by Poletti et al. 2011, but items 29 (gait) and 30 (postural stability) were excluded since those are included in the PIGD score. Overall NMS severity was assessed using the Non-Motor Symptoms Scale (NMSS). The degree of constipation was quantified in more detail using the Wexner constipation score. Diagnosis of active irritable bowel syndrome (IBS) was an exclusion criterion in this study since it is associated with alterations of gut microbiota.

Analysis of Fecal Microbiota

Sample Collection

The subjects collected the fecal samples at home into collection tubes pre-filled with Stool DNA Stabilizer (PSP® Spin Stool DNA Plus Kit, STRATEC Molecular). Within three days, the tubes were transferred to a storing temperature of −80° C. until further processing.

DNA Extraction and PCR

Total DNA was extracted using the PSP® Spin Stool DNA Plus Kit (STRATEC Molecular). PCR amplification was carried out in an ARKTIK Thermal Cycler (Finnzymes Diagnostics/Thermo Scientific). In the first stage, the V1-V3 regions of the bacterial 16S rRNA gene were amplified in three replicate reactions with universal bacterial primers pA (AGAGTTTGATCMTGGCTCAG)(SEQ ID NO:1) and pD' (GTATTACCGCGGCTGCTG)(SEQ ID NO:2) with 18-mer overhangs added to the 5' ends of the primers (Edwards et al., 1989; Lane et al. 1991). The replicate PCR products were pooled and purified with Agencourt® AMPure® XP magnetic beads (Agencourt Bioscience) and subjected to a second PCR round with barcoded forward primers and a reverse primer, both of which attached to the respective 18-mer overhang sequences from the primers of the first PCR amplification. Phusion polymerase (Thermo Fisher Scientific/Finnzymes) with HF buffer and 2.5% DMSO were used. Cycling conditions for both PCR reactions consisted of an initial denaturation at 98° C. for 30 s, followed by 15 cycles at 98° C. for 10 s, 65° C. for 30 s, and 72° C. for 10 s, and then a final extension for 5 min. Between 3.6 and 60 ng of template DNA were used in the initial reaction. DNA concentration and quality were measured with Qubit (Invitrogen) and Bioanalyzer 2100 (Agilent).

Sequencing and Sequence Quality Control

PCR products were sequenced using 454-GS FLX Titanium chemistry, with an average read length of ~400 bp (Roche Diagnostics). The dataset consisted of 2549217 raw reads (mean read count 17224 per subject). Basic sequence quality control and taxonomical assignment were performed with mothur, following the standard operating procedure for 454 sequenced 16S data (Schloss et al., 2011). The phylotype based approach was selected for further analysis. The final dataset included 1131504 reads, with a mean read count of 7645 per subject, and a mean read length of 218 bases. The sequences have been deposited in the Sequence Read Archive at the European Bioinformatics Institute (accession no. PRJEB4927).

Statistical Analysis

From each subject, random subsamples of 4500 sequences were used for statistical analysis of family level data. Alpha diversity indices were calculated and beta diversity dendrograms describing the between subject differences were generated and compared with mothur. Differences in bacterial communities between patients and controls and between PIGD and TD patients (a priori defined subgroup analysis) were analyzed using Metastats (White et al., 2009). The following analyses were performed using IBM® SPSS® Statistics Version 19.0.0.1 (IBM Corp.): Group differences of clinical parameters were analyzed using T-tests for normally distributed variables, otherwise non-parametric tests were used. Differences regarding categorical variables were tested using Fisher's exact test. Associations of microbiome features with clinical parameters were explored using generalized linear models (GLM) employing linear, negative binomial, or logistic distributions depending on the distribution of the target variable.

In the Metastats results, differences with Q-values below 0.05 were considered significant and are the basis of the main conclusions of this paper. We also performed exploratory analyses on bacterial families with higher Q-values if P-values were below 0.05. In the remaining analyses (SPSS), P-values below 0.05 (two-sided if not indicated otherwise) were considered significant.

Results

Demographics and Clinical Data

The patient and control groups were similar with respect to most of the studied variables (Tables 1).

TABLE 1

Selected demographic and clinical parameters of the cohort including all those parameters that showed significantly different distributions between groups.

| | Patients | Controls | P-Value |
|---|---|---|---|
| Demographics | | | |
| n | 72 | 72 | |
| female subjects | 48.6% | 50.0% | 1.000 |
| Age (years, mean ± SD) | 65.3 ± 5.5 | 64.5 ± 6.9 | 0.448 |
| Medical History | | | |
| Atrial Fibrillation | 4.2% | 18.1% | 0.015 |
| TIA or Ischaemic Stroke | 7.0% | 37.5% | <0.001 |
| Non-motor Symptoms | | | |
| Overall NMS severity (NMSS | 40 [25.25-55.00] | 8 [4.00-11.75] | <0.001 |
| Constipation (Wexner score) | 5 [3-9] | 2 [1-4] | <0.001 |
| Medication | | | |
| Levodopa | 54.2% | 0% | <0.001 |
| COMT Inhibitor | 15.3% | 0% | 0.001 |
| Dopamine Agonist | 77.8% | 0% | <0.001 |
| MAO Inhibitor | 70.8% | 0% | <0.001 |
| Anticholinergic | 8.3% | 0% | 0.028 |
| Warfarin | 1.4% | 15.3% | 0.004 |
| Statin | 20.8% | 54.2% | <0.001 |

A dopamine transporter SPECT study was documented for 26 (36.1%) patients (TD: 56.5%, MX: 22.2%, PIGD: 27.5%). For 14 (19.4%) patients it was not known whether a SPECT study had been performed at time of diagnosis. The median of the time from motor symptom onset to study visit was 5 [3-8] years (TD: 5 [3-6], MX: 6 [2-12.5], PIGD: 6 [3-10]). The median H&Y stage was 2.5 [2.0-2.5] (Table 2).

TABLE 2

Distribution of PD patients into the modified Hoehn & Yahr (H&Y) stages

| | H&Y Stage | | | | |
|---|---|---|---|---|---|
| | 1 | 1.5 | 2 | 2.5 | 3 |
| n (%) | 4 (5.6%) | 2 (2.8%) | 23 (31.9%) | 27 (37.5%) | 16 (22.2%) |

The mean (±SD) scores for total UPDRS and UPDRS-III were 45.5±13.6 and 31.6±9.0 points, respectively. 97.3% of PD patients were using antiparkinsonian medication (Table 1). Two patients (2.8%) were treated by deep brain stimulation (DBS). 55.6% of our patients had a PIGD phenotype, 31.9% were TD, and 12.5% were classified as MX. PD patients had significantly more severe NMS overall (median NMSS score 40 [25.25-55.00] vs. 8 [4.00-11.75] points; P<0.001) and constipation in particular than control subjects (median Wexner constipation score 5 [3-9] vs. 2 [1-4] points; P<0.001).

Microbiome

Figure 1:
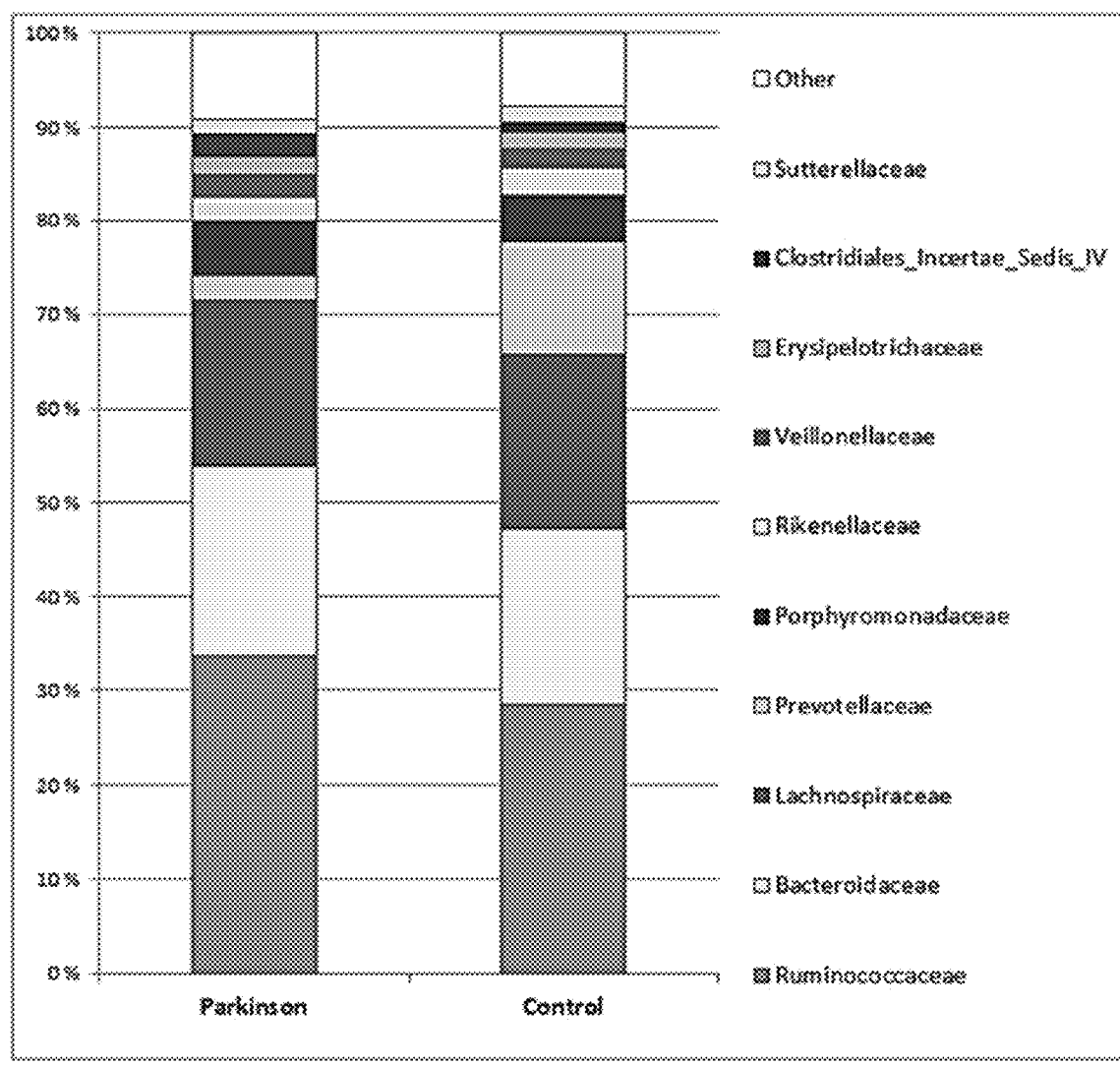
FIG. 1 shows relative abundances of the 10 most abundant bacterial families in the subsampled dataset.

The full dataset included bacteria from 360 genera, 125 families, 60 orders, 29 classes and 18 phyla. The majority of the reads (94%) represented the phyla Firmicutes and Bacteroidetes, which are typically the dominant phyla in the gut microbiome. In the subsampled dataset the 10 and 5 most common families accounted for 91.6% and 81.3% of all reads, respectively (FIG. 1). While no statistically significant differences were found with respect to commonly used alpha diversity indices (Chao1, ACE, Shannon, Inverse Simpson, data not shown), comparisons of the clustering of patient and control samples in dendrograms based on beta diversity metrics (Yue & Clayton theta, Morisita-Horn index and Bray-Curtis index, calculated with family-level data) showed a significant difference between groups (unweighted UniFrac P<0.02 and weighted UniFrac P<0.001 for all three indices).

Figure 2:
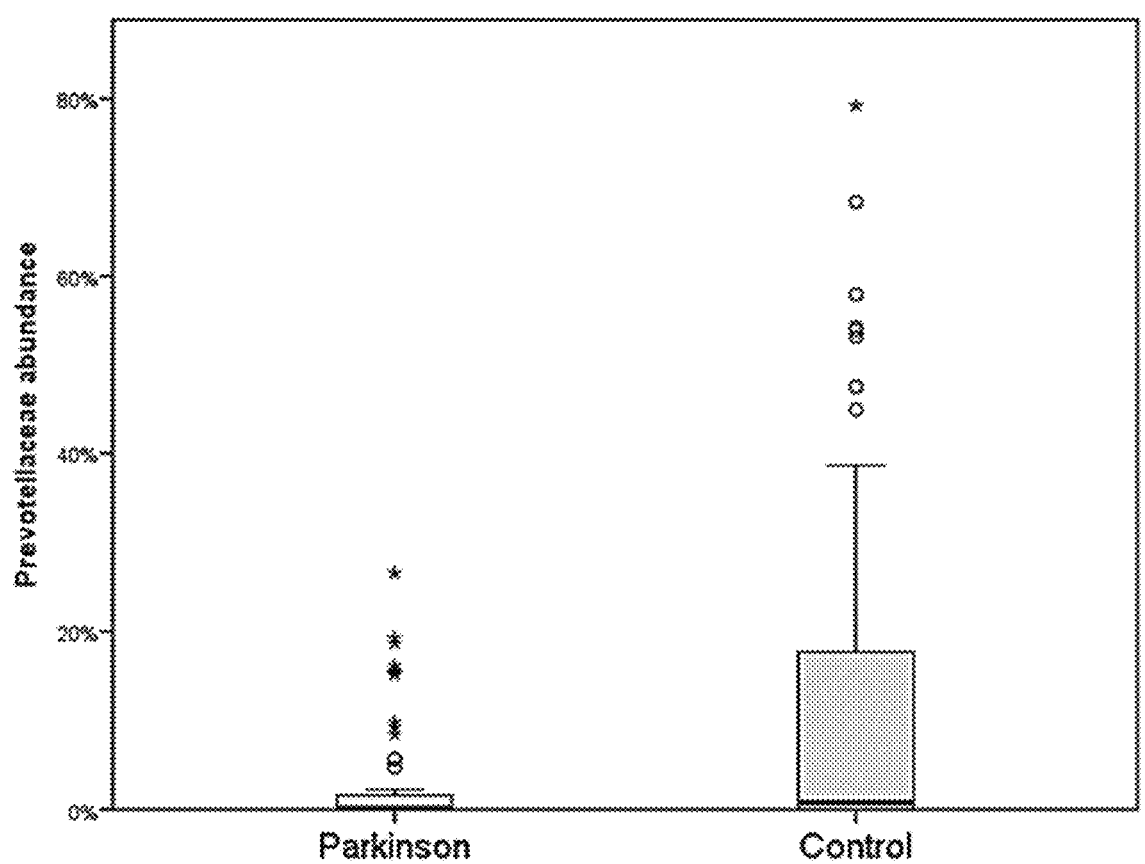
FIG. 2 shows distributions of Prevotellaceae abundance in both study groups

The mean abundance of Prevotellaceae in the feces of PD subjects was reduced by 77.6% in comparison to control subjects (Q=0.031; Table 3). High levels of Prevotellaceae were rare in the PD group whereas low levels were found in both groups (FIG. 2). Samples devoid of Prevotellaceae were equally frequent in both groups (PD: 29.2%; control: 27.8%; P=1.000; Fisher's exact test). The explorative analysis suggested that five families were more abundant in patients than in controls, but the absolute differences between groups were smaller than for Prevotellaceae (Table 3).

TABLE 3

Bacterial families showing different abundances between PD and control groups with a P-value less than 0.05.

| Taxonomy | Patients* | Controls* | P-Value | Q-Value |
|---|---|---|---|---|
| Prevotellaceae | 2.70 ± 0.32 | 12.06 ± 3.73 | 0.001 | 0.031 |
| Lactobacillaceae | 0.44 ± 0.04 | 0.02 ± 0.00 | 0.004 | 0.063 |
| Verrucomicrobiaceae | 0.06 ± 0.00 | 0.02 ± 0.00 | 0.014 | 0.146 |
| Bradyrhizobiaceae | 0.16 ± 0.00 | 0.03 ± 0.00 | 0.021 | 0.151 |
| Clostridiales Incertae Sedis IV | 2.49 ± 0.30 | 1.01 ± 0.03 | 0.025 | 0.151 |
| Ruminococcaceae | 33.63 ± 1.99 | 28.54 ± 1.81 | 0.029 | 0.151 |

*mean % ± variance

Mean abundance and variation of taxa at the genus level (Table 4a) and family level (Table 4b) that showed different abundances in PD and control groups (Metastats analysis) are shown in Table 4a and b. Data is based on same sample as family data.

TABLE 4a

Mean abundance and variation of taxa at the genus level that showed different abundances in PD and control groups

| | Parkinson | | | Control | | | | |
|---|---|---|---|---|---|---|---|---|
| Genus | mean (group1) | variance (group1) | stderr (group1) | mean (group2) | variance (group2) | stderr (group2) | p-value | q-value |
| Prevotella | 0.013423 | 0.001995 | 0.005264 | 0.104250 | 0.035548 | 0.022220 | 0.000999 | 0.021104 |
| Lactobacillus | 0.004358 | 0.000390 | 0.002329 | 0.000216 | 0.000001 | 0.000087 | 0.000999 | 0.021104 |
| Saccharofennentans | 0.047272 | 0.002385 | 0.005755 | 0.029738 | 0.000912 | 0.003560 | 0.016983 | 0.198570 |
| Anaerotruncus | 0.024364 | 0.000787 | 0.003307 | 0.015238 | 0.000310 | 0.002074 | 0.018981 | 0.198570 |
| Mahella | 0.025262 | 0.003024 | 0.006480 | 0.010022 | 0.000322 | 0.002114 | 0.020979 | 0.198570 |
| Sutterella | 0.005485 | 0.000075 | 0.001019 | 0.010182 | 0.000217 | 0.001735 | 0.020979 | 0.198570 |
| Agromonas | 0.001469 | 0.000021 | 0.000545 | 0.000306 | 0.000001 | 0.000144 | 0.022977 | 0.198570 |
| Phaeovibrio | 0.003355 | 0.000175 | 0.001561 | 0.000438 | 0.000003 | 0.000203 | 0.041958 | 0.332389 |

TABLE 4b

Mean abundance and variation of taxa at the family level that showed different abundances in PD and control groups

| | Parkinson | | | Control | | | | |
|---|---|---|---|---|---|---|---|---|
| Taxonomy | mean (group1) | variance (group1) | stderr (group1) | mean (group2) | variance (group2) | stderr (group2) | p-value | q-value |
| Prevotellaceae | 0.0270 | 0.0032 | 0.0066 | 0.1206 | 0.0373 | 0.0228 | 0.0010 | 0.0313 |
| Lactobacillaceae | 0.0044 | 0.0004 | 0.0023 | 0.0002 | 0.0000 | 0.0001 | 0.0040 | 0.0627 |
| Verrucomicrobiaceae | 0.0006 | 0.0000 | 0.0002 | 0.0002 | 0.0000 | 0.0000 | 0.0140 | 0.1462 |

TABLE 4b-continued

Mean abundance and variation of taxa at the family level that showed different abundances in PD and control groups

| Taxonomy | Parkinson | | | Control | | | | |
| --- | --- | --- | --- | --- | --- | --- | --- | --- |
| | mean (group1) | variance (group1) | stderr (group1) | mean (group2) | variance (group2) | stderr (group2) | p-value | q-value |
| Bradyrhizobiaceae | 0.0016 | 0.0000 | 0.0006 | 0.0003 | 0.0000 | 0.0001 | 0.0210 | 0.1514 |
| Clostridiales_Incertae_Sedis_IV | 0.0249 | 0.0030 | 0.0065 | 0.0101 | 0.0003 | 0.0022 | 0.0250 | 0.1514 |
| Ruminococcaceae | 0.3363 | 0.0199 | 0.0166 | 0.2854 | 0.0181 | 0.0158 | 0.0290 | 0.1514 |

It was investigated whether antiparkinsonian inculcation was a possible confounder by testing each of the abovementioned families for significantly different abundances between users and non-users of each antiparkinsonian drug class in the PD group. Patients using COMT-inhibitors had significantly higher levels (median % [IQR]) of Lactobacillaceae (0.22 [0-2.07] vs. 0 [0-0.02]; P=0.001) and lower levels of Clostridiales Incertae Sedis IV (0.00 [0-0.20] vs. 0.84 [0.02-2.73]; P=0.005) than those not using this class of drugs. No significant differences were found for any other antiparkinsonian drug class.

To estimate effects of possible confounders (Table 1) on the observed group differences GLMs was applied to model the distribution of bacterial abundances (Table 5). For those bacterial families that were more abundant in PD subjects, Prevotellaceae abundance was also included in the model to disentangle a group related effect from an unspecific effect compensating low Prevotellaceae levels. Study group was the only factor that was significantly associated with Prevotellaceae abundance (Table 5). Thus, the decreased abundance of Prevotellaceae was not explained by e.g. more severe constipation in the PD group or differences in medications or medical history. The abundances of all the other families except for Ruminococcaceae were independently related to PD diagnosis. Ruminococcaceae abundance was significantly associated only with levels of Prevotellaceae suggesting that the higher levels of Ruminococcaceae in the PD group were not related to PD itself, but rather compensating lower levels of Prevotellaceae (Table 5). Abundances of Verrucomicrobiaceae and Bradyrhizobiaceae were associated with the severity of NMS and in particular constipation. Abundances of Lactobacillaceae, Bradyrhizobiaceae, and Clostridiales Incertae Sedis IV were associated with statin medication and abundance of Lactobacillaceae also with previous TIA/ischaemic stroke. The independent associations of bacterial abundances with PD diagnosis remained significant when subjects fulfilling Rome-III criteria for IBS were excluded from the analysis.).

TABLE 5

GLM results
Results of the GLMs for bacterial abundances (sequence counts) based on the group factor and possible confounders. Normal distribution for Ruminococcaceae. Negative binomial distribution with log link for all others. COMT-inhibitor medication effect was nested within the study group effect for Lactobacillaceae and Clostridiales Incertae Sedis IV. Results shown as: B [95% CI], Wald Chi-Square, P-Value

| Family | Control vs. PD | Atrial fibrillation No vs. Yes | TIA or ischaemic stroke No vs. Yes | Warfarin No vs. Yes | Statin No vs. Yes |
| --- | --- | --- | --- | --- | --- |
| Prevotellaceae | 1.490 [1.005-1.976], 36.179, <0.001 | 0.432 [−0.489-1.353], 0.845, 0.358 | 0.025 [−0.517-0.567], 0.008, 0.927 | −0.145 [−1.218-0.928], 0.070, 0.791 | −0.096 [−0.542-0.349], 0.180, 0.671 |
| Lactobacillaceae | −5.095 [−6.190--4.000], 83.151, <0.001 | 0.017 [−1.502-1.535], 0.000, 0.983 | 1.754 [0.958-2.549], 18.667, <0.001 | −0.258 [−1.943-1.427], 0.090, 0.764 | −1.859 [−2.373--1.344], 50.134, <0.001 |
| Verrucomicrobiaceae | −1.126 [−1.784--0.468], 11.254, 0.001 | 1.031 [−0.714-2.775], 1.341, 0.247 | 0.228 [−0.475-0.931], 0.405, 0.525 | −1.768 [−3.654-0.117], 3.378, 0.066 | 0.081 [−0.496-0.658], 0.076, 0.783 |
| Bradyrhizobiaceae | −2.368 [−3.069--1.666], 43.748, <0.001 | −0.109 [−1.307-1.088], 0.032, 0.858 | −0.440 [−1.237-0.356], 1.174, 0.279 | −0.213 [−1.631-1.204], 0.087, 0.768 | 0.687 [0.004-1.370], 3.891, 0.049 |
| Clostridiales Incertae Sedis IV | 1.441 [0.613-2.269], 11.628, 0.001 | 0.173 [−0.418-0.764], 0.330, 0.565 | −0.080 [−0.549-0.388], 0.113, 0.737 | 0.481 [−0.208-1.170], 1.871, 0.171 | −0.856 [−1.303--0.409], 14.116, <0.001 |
| Ruminococcaceae | −52.526 [−317.204-212.151], 0.151, 0.697 | −243.780 [−719.394-231.834], 1.009, 0.315 | 96.856 [−175.166-368.877], 0.487, 0.485 | 190.885 [−347.816-729.585], 0.482, 0.487 | −112.421 [−339.258-114.416], 0.944, 0.331 |

| Family | | Total NMSS Score (Z-transformed) | Total Wexner Score (Z-transformed) | Prevotellaceae abundance (Z-transformed) | COMT-inhibitor No vs. Yes |
| --- | --- | --- | --- | --- | --- |
| Prevotellaceae | | 0.038 [−0.154-0.230], 0.152, 0.696 | −0.040 [−0.270-0.191], 0.114, 0.736 | | |
| Lactobacillaceae | | −0.199 [−0.590-0.193], 0.988, 0.320 | −0.015 [−0.280-0.250], 0.012, 0.911 | 0.377 [0.142-0.611], 9.925, 0.002 | −3.998 [−4.756--3.241], 107.025, <0.001 |

TABLE 5-continued

GLM results
Results of the GLMs for bacterial abundances (sequence counts) based on the group factor and possible confounders. Normal distribution for Ruminococcaceae. Negative binomial distribution with log link for all others. COMT-inhibitor medication effect was nested within the study group effect for Lactobacillaceae and Clostridiales Incertae Sedis IV. Results shown as: B [95% CI], Wald Chi-Square, P-Value

| | | | | |
|---|---|---|---|---|
| Verrucomicrobiaceae | −0.340 [−0.626−−0.054], 5.444, 0.020 | 0.406 [0.141-0.672], 9.001, 0.003 | −0.954 [−1.523−−0.385], 10.801, 0.001 | |
| Bradyrhizobiaceae | −0.376 [−0.703−−0.049], 5.076, 0.024 | −0.595 [−0.888−−0.301], 15.769, <0.001 | −0.285 [−0.618-0.048], 2.813, 0.094 | |
| Clostridiales Incertae Sedis IV | −0.144 [−0.397−0.109], 1.239, 0.266 | 0.153 [−0.074-0.380], 1.742, 0.187 | −0.712 [−0.938−−0.485], 37.966, <0.001 | 2.237 [1.557-2.918], 41.535, <0.001 |
| Ruminococcaceae | −27.605 [−157.321-102.112], 0.174, 0.677 | 95.836 [−16.063-207.736], 2.818, 0.093 | −212.358 [−311.798−−112.917], 17.519, <0.001 | |

A receiver operating characteristic (ROC) curve analysis of Prevotellaceae abundance was performed with respect to discrimination between PD patients and controls (FIG. 3). Using the optimal inclusive cut-off of 6.5% for classifying a subject with low Prevotellaceae abundance into the PD group, PD patients were identified with 86.1% sensitivity but only 38.9% specificity (LR+=1.41, LR−=0.36). It was evaluated whether inclusion of other bacterial families improved the discriminative power by performing a logistic regression analysis with study group as the dependent variable and all six bacterial families as covariates (likelihood ratio based backward elimination method). This model retained Prevotellaceae, Lactobacillaceae, Bradyrhizobiaceae and Clostridiales Incertae Sedis IV as predictors of study group (Table 6).

TABLE 6

Logistic Regression
Results of logistic regression analysis with study group as the dependent variable. Initially all six bacterial families were included as covariates. We employed a backward elimination method based on the likelihood ratio.

| Covariate | Wald | P-Value | OR per 1% increase in abundance for belonging to PD group [95% CI] |
|---|---|---|---|
| Prevotellaceae | 7.478 | 0.006 | 0.945 [0.907-0.984] |
| Lactobacillaceae | 1.805 | 0.179 | 23.441 [0.235-2337.377] |
| Bradyrhizobiaceae | 3.965 | 0.046 | 15.788 [1.044-238.716] |
| Clostridiales Incertae Sedis IV | 2.166 | 0.141 | 1.112 [0.966-1.280] |

This classifier (FIG. 3) achieved a significantly higher AUC than Prevotellaceae alone (P=0.020 one-sided) and provided 90.3% specificity and 47.2% sensitivity (optimal probability cut-off 0.54; LR+=4.86, LR−=0.58). When Wexner total score as a clinical measure of constipation was included (Table 7) the discriminative power was further increased significantly (P=0.022 one-sided) due to better sensitivity (66.7%) and preserved 90.3% specificity (optimal probability cut-off 0.55; LR+=6.86, LR−=0.37; FIG. 3). The AUC of this model was also larger than that of Wexner score alone, but this difference just missed the level of significance (P=0.055 one-sided).

TABLE 7

Logistic Regression
Results of logistic regression analysis with study group as the dependent variable after adding Wexner constipation score to the model. Based on Z-transformed values.

| Covariate | Wald | P-Value | OR per 1 unit Z-score increase for belonging to PD group [95% CI] |
|---|---|---|---|
| Prevotellaceae | 7.053 | 0.008 | 0.429 [0.230-0.801] |
| Lactobacillaceae | 1.752 | 0.186 | 156.372 [0.088-277179.530] |
| Bradyrhizobiaceae | 3.562 | 0.059 | 2.590 [0.964-6.957] |
| Clostridiales Incertae Sedis IV | 1.084 | 0.298 | 1.349 [0.768-2.371] |
| Wexner total score | 17.742 | <0.001 | 2.969 [1.789-4.927] |

Enterobacteriaceae were significantly more abundant in patients with a PIGD phenotype than in TD patients (Q=0.018; FIG. 4, Table 8).

TABLE 8

Bacterial families showing differences in abundances between TD and PIGD phenotypes with a p-value less than 0.05.

| Taxonomy | TD* | PIGD* | P-Value | Q-Value |
|---|---|---|---|---|
| Enterobacteriaceae | 0.28 ± 0.00 | 2.31 ± 0.26 | 0.004 | 0.018 |
| Erysipelotrichaceae | 1.17 ± 0.02 | 2.19 ± 0.04 | 0.024 | 0.103 |

*mean % ± variance

Potential confounders such as gender ratio, medical history, medication, Wexner score, or time from motor symptom onset did not differ significantly between TD and PIGD subgroups. However, PIGD subjects tended to be older (66.3±5.7 vs. 63.4±5.2 years; mean±SD; P=0.051) and to have higher NMSS total scores (42.0 [32.0-69.5] vs. 33.0 [19.0-51.0]; P=0.053) than TD subjects. The only antiparkinsonian drug class significantly associated with Enterobacteriaceae abundance was COMT-inhibitors (users: 0.56 [0.24-7.40]; non-users: 0.09 [0.02-0.62]; median % [IQR]; P=0.043). A GLM was used to quantify effects of these possible confounders versus the effect of PD phenotype on Enterobacteriaceae abundance. In this model, PIGD and akinetic-rigid subscores, were positively associated with Enterobacteriaceae abundance whereas the negative association with tremor subscore slightly missed the level of significance (Table 9). When patients with motor fluctuations or DBS treatment were excluded from the analysis (n=43; Table 9), the association with PIGD subscore remained highly significant, but not the association with akinetic-rigid subscore. However, in this model the COMT-inhibitor medication showed a positive association with Enterobacteriaceae abundance.

TABLE 9

GLM results
Results of the GLMs for Enterobacteriaceae abundance (sequence counts) based on phenotype subscores and possible confounders. Negative binomial distribution with log link. Results shown as: B [95% CI], Wald Chi-Square, P-Value

|  | Tremor subscore (Z-transformed) | PIGD subscore (Z-transformed) | Akinetic rigid subscore (Z-transformed) | NMSS total score (Z-transformed) | Age (Z-transformed) | COMT-inhibitor No vs. Yes |
|---|---|---|---|---|---|---|
| Enterobacteriaceae (all patients included; n = 72) | −0.254 [−0.517−−0.009], 3.572, 0.059 | 0.931 [0.500-1.362], 17.955, <0.001 | 0.445 [0.134-0.757], 7.857, 0.005 | −0.237 [−0.638-0.164], 1.340, 0.247 | 0.156 [−0.150-0.462], 0.996, 0.318 | −0.712 [−1.495-0.071], 3.173, 0.075 |
| Enterobacteriaceae (motor fluctuations and DBS excluded; n = 43) | −0.143 [−0.619-0.332], 0.349, 0.555 | 2.643 [1.698-3.588], 30.075, <0.001 | −0.210 [−0.695-0.274], 0.724, 0.395 | −0.344 [−1.065-0.377], 0.876, 0.349 | −0.366 [−0.920-0.188], 1.676, 0.196 | −3.502 [−5.836−−1.167], 8.643, 0.003 |

TABLE 10

Mean abundance and variation of taxa at the genus level that showed different abundances in TD and PIGD groups

|  | TD | | | PIGD | | | | |
|---|---|---|---|---|---|---|---|---|
| Taxonomy | mean (group1) | variance (group1) | stderr (group1) | mean (group2) | variance (group2) | stderr (group2) | p-value | q-value |
| *Clostridium* XVIII | 0.001585 | 0.000002 | 0.000292 | 0.004567 | 0.000046 | 0.001068 | 0.000999 | 0.002519 |
| *Anaerofilum* | 0.000213 | 0 | 0.000038 | 0.000456 | 0 | 0.000071 | 0.002997 | 0.007337 |
| *Papillibacter* | 0.000976 | 0.000001 | 0.000215 | 0.003389 | 0.000036 | 0.000953 | 0.006993 | 0.016638 |
| *Succiniclasticum* | 0 | 0 | 0 | 0.000617 | 0.000014 | 0.000588 | 0.006993 | 0.016638 |
| *Klebsiella* | 0 | 0 | 0 | 0.001206 | 0.000018 | 0.000677 | 0.008991 | 0.021095 |
| *Escherichia_Shigella* | 0.002966 | 0.000044 | 0.00139 | 0.02115 | 0.002558 | 0.007997 | 0.017982 | 0.03997 |
| *Paludibacter* | 0.000348 | 0.000001 | 0.000162 | 0.003461 | 0.000147 | 0.001916 | 0.020979 | 0.04486 |
| *Anaerostipes* | 0.00257 | 0.000016 | 0.00083 | 0.00055 | 0.000001 | 0.000183 | 0.020979 | 0.04486 |

It was found that, although no subject had a known diagnosis of active irritable bowel syndrome (IBS), 18 of 72 (25.0%) of PD patients but only 4 of 72 (5.6%) of control subjects fulfilled Rome-III criteria for IBS (Fisher's exact test p=0.002). While this prevalence in the control group matched that reported in previous studies, this is the first documentation of a clearly increased prevalence of IBS symptoms in PD patients indicating that IBS may be a non-motor symptom of PD.

REFERENCES

Savica R, Carlin J M, Grossardt B R et al. Medical records documentation of constipation preceding parkinson disease: A case-control study. Neurology 2009; 73(21):1752-1758.
Noyce A J, Bestwick J P, Silveira-Moriyama L et al. Meta-analysis of early nonmotor features and risk factors for parkinson disease. Ann Neurol 2012; 72(6):893-901.
Kieburtz K, Wunderle K B. Parkinson's disease: Evidence for environmental risk factors. Mov Disord 2013; 28(1): 8-13.
de Vos W M, de Vos E A. Role of the intestinal microbiome in health and disease: From correlation to causation. Nutr Rev 2012; 70 Suppl 1:S45-56.
Segata N, Izard J, Waldron L, Gevers D, Miropolsky L, Garrett W S, Huttenhower C. Metagenomic biomarker discovery and explanation. Genome Biol. 2011 Jun. 24; 12(6):R60. doi: 10.1186/gb-2011-12-6-r60.
Arumugam M, Raes J, Pelletier E et al. Enterotypes of the human gut microbiome. Nature 2011; 473(7346): 174-180.
Jankovic J, McDermott M, Carter J et al. Variable expression of parkinson's disease: A base-line analysis of the DATATOP cohort. the parkinson study group. Neurology 1990; 40(10): 1529-1534.
Poletti M, Frosini D, Pagni C et al. The association between motor subtypes and alexithymia in de novo parkinson's disease. J Neurol 2011; 258(6):1042-1045.
Edwards U, Rogall T, Blocker H et al. Isolation and direct complete nucleotide determination of entire genes. characterization of a gene coding for 16S ribosomal RNA. Nucleic Acids Res 1989; 17(19):7843-7853.
Lane D J. 16S/23S rRNA sequencing. In: Stackebrandt, E. Goodfellow, M. Eds. Nucleic Acid Techniques in Bacterial Systematics. 1991; p 115-175.
Schloss P D, Westcott S L, Ryabin T et al. Introducing mothur: Open-source, platform-independent, community-supported software for describing and comparing microbial communities. Appl Environ Microbiol 2009; 75(23): 7537-7541.
White J R, Nagarajan N, Pop M. Statistical methods for detecting differentially abundant features in clinical metagenomic samples. PLoS Comput Biol 2009; 5:e1000352.

The invention claimed is:

1. A method for treatment or prevention of Parkinson's disease (PD) in an individual, comprising administering to said individual a composition that increases the abundance of Prevotellaceae in the intestine, wherein active ingredients of the composition consist of Prevotellaceae.

2. The method of claim 1, wherein the composition comprises live or killed microbes.

3. The method of claim 1, wherein the composition is in the form of a food composition, pharmaceutical composition, nutraceutical, supplement or an anaerobical microbiota culture.

4. The method of claim 1, wherein the composition comprises Prevotella.

5. The method of claim 4, wherein the composition comprises one or more Prevotella genera selected from the group consisting of Prevotella amnii, Prevotella bergensis, Prevotella bivia, Prevotella bryantii, Prevotella buccae, Prevotella buccalis, Prevotella copri, Prevotella coprocola, Prevotella disiens, Prevotella marshii, Prevotella melaninogenica, Prevotella oralis, Prevotella oris, Prevotella ruminicola, Prevotella salivae, Prevotella sp, Prevotella sp oral taxon 299, Prevotella sp oral taxon 317, Prevotella sp oral taxon 472, Prevotella tannerae, Prevotella timonensis and Prevotella veroralis.

6. The method of claim 1, wherein the composition decreases intestinal abundance of one or more of taxa selected from the group consisting of Lactobacillaceae, Verrucomicrobiaceae, Bradyrhizobiaceae, Clostridiales Incertae Sedis IV, Ruminococcaceae, Lachnospiraceae, Enterobacteriaceae, Bacteroidaceae, Alistipes, Coprococcus, Anaerotruncus, Porphyromonadaceae, Parabacteroides, Butyricicoccus, Collinsella, Eggerthella, Coriobacteriaceae, Sporobacterium, Actinobacteria, Blautia, Enterococcus, Acetivibrio, Allobaculum, Agromonas, Firmicutes, Mahella, Phaeovibrio, Porphyromonadaceae, Oscillibacter and Saccharofermentans.

7. The method of claim 1, wherein the individual is diagnosed with PD.

8. The method of claim 1, wherein the individual has a high probability developing or having PD, wherein the individual has a low relative abundance of Prevotellaceae and/or Prevotella.

9. The method of claim 8, wherein the individual has a low relative abundance of Prevotellaceae and/or a high relative abundance of one or more of taxa selected from the group consisting of Lactobacillaceae, Verrucomicrobiaceae, Bradyrhizobiaceae, Clostridiales Incertae Sedis IV, Ruminococcaceae, Lachnospiraceae, Enterobacteriaceae, Bacteroidaceae, Alistipes, Coprococcus, Anaerotruncus, Porphyromonadaceae, Parabacteroides, Butyricicoccus, Collinsella, Eggerthella, Coriobacteriaceae, Sporobacterium, Actinobacteria, Blautia, Enterococcus, Acetivibrio, Allobaculum, Agromonas, Firmicutes, Mahella, Phaeovibrio, Porphyromonadaceae, Oscillibacter and Saccharofermentans.

10. The method of claim 8, wherein the individual is not diagnosed with PD.

11. The method of claim 9, wherein the individual is not diagnosed with PD.

12. The method of claim 1, wherein the composition is administered mixed in food or drink or separately in the form of a tablet, capsule, microcapsule, powder, solution or paste.

13. The method of claim 12, wherein the food is a food supplement, a formula for nutritional purposes, or a nutraceutical, and/or wherein the food optionally contains additives and excipients.

14. The method of claim 4, wherein the Prevotella comprises one or more species of Prevotella disiens, Prevotella oris, or Prevotella melaninogenica.

15. The method of claim 1, wherein active ingredients of the composition consist of one or more species of Prevotella disiens, Prevotella oris, or Prevotella melaninogenica.

* * * * *

SEQUENCE LISTING

```
Sequence total quantity: 2
SEQ ID NO: 1            moltype = DNA   length = 20
FEATURE                 Location/Qualifiers
source                  1..20
                        mol_type = other DNA
                        organism = synthetic construct
SEQUENCE: 1
agagtttgat cmtggctcag                                                   20

SEQ ID NO: 2            moltype = DNA   length = 18
FEATURE                 Location/Qualifiers
source                  1..18
                        mol_type = other DNA
                        organism = synthetic construct
SEQUENCE: 2
gtattaccgc ggctgctg                                                     18
```